(12) United States Patent  (10) Patent No.: US 9,354,152 B2
Yuan  (45) Date of Patent: May 31, 2016

(54) RHEOMETRY APPARATUS

(75) Inventor: Xue-Feng Yuan, Manchester (GB)

(73) Assignee: The University of Manchester, Manchester (GB)

( * ) Notice: Subject to any disclaimer, the term of this patent is extended or adjusted under 35 U.S.C. 154(b) by 494 days.

(21) Appl. No.: 13/813,933

(22) PCT Filed: Aug. 3, 2011

(86) PCT No.: PCT/GB2011/051476
§ 371 (c)(1),
(2), (4) Date: Feb. 1, 2013

(87) PCT Pub. No.: WO2012/017246
PCT Pub. Date: Feb. 9, 2012

(65) Prior Publication Data
US 2013/0125627 A1    May 23, 2013

(30) Foreign Application Priority Data

Aug. 3, 2010 (GB) .................................. 1013044.1

(51) Int. Cl.
*G01N 11/08* (2006.01)

(52) U.S. Cl.
CPC ........... *G01N 11/08* (2013.01); *Y10T 29/49826* (2015.01)

(58) Field of Classification Search
CPC .................................................. G01N 11/08
See application file for complete search history.

(56) References Cited

U.S. PATENT DOCUMENTS

| 3,952,577 A | 4/1976 | Hayes et al. | |
|---|---|---|---|
| 4,425,790 A * | 1/1984 | Bice et al. | 73/54.05 |
| 4,573,345 A | 3/1986 | Krutchen et al. | |
| 6,386,016 B1 | 5/2002 | Gleissle | |
| 6,915,679 B2 * | 7/2005 | Chien et al. | 73/54.01 |

(Continued)

FOREIGN PATENT DOCUMENTS

DE    3818941 A1    12/1989

OTHER PUBLICATIONS

International Preliminary Report on Patentability and Written Opinion for International Application No. PCT/GB2011/051476 mailed Mar. 19, 2013. 7 pages.

(Continued)

*Primary Examiner* — John Fitzgerald
(74) *Attorney, Agent, or Firm* — Wilmer Cutler Pickering Hale and Dorr LLP

(57) ABSTRACT

Rheometry apparatus comprises a block of substantially rigid material having an external surface and at least a first internal flow channel, the first internal flow channel being arranged inside the block and substantially in a plane and the block further comprising a plurality of holes, each hole communicating with the first internal flow channel at a respective position along the first internal flow channel and extending from the respective position to said external surface so as to provide access to the first internal flow channel from the external surface, the plurality of holes comprising a first hole communicating with a first said position, for connection to pumping means to drive fluid flow along said first internal flow channel, a second hole communicating with a second position and in which a sensor may be located to measure a property of fluid at the second position, and a third hole communicating with a third position and in which a sensor may be located to measure a property of fluid at the third position.

51 Claims, 15 Drawing Sheets

(56) References Cited

U.S. PATENT DOCUMENTS

| | | | |
|---|---|---|---|
| 7,143,637 B1 | 12/2006 | McBrearty et al. | |
| 7,290,441 B2 * | 11/2007 | Baek | 73/54.09 |
| 8,518,309 B2 * | 8/2013 | Maris-Haug et al. | 264/40.1 |
| 2004/0154383 A1 * | 8/2004 | Woolf et al. | 73/53.01 |
| 2005/0005684 A1 * | 1/2005 | Chien et al. | 73/54.01 |
| 2005/0183496 A1 | 8/2005 | Baek | |
| 2008/0134765 A1 | 6/2008 | Baek | |

OTHER PUBLICATIONS

Whiteside, G. M. "The Origins and the Future of Microfluidics", Nature, vol. 442, 27, Jul. 2006, pp. 368-373.

* cited by examiner

RHEOMETRY APPARATUS

RELATED APPLICATIONS

This application is a §371 of International Patent Application No. PCT/GB2011/051476 filed Aug. 3, 2011, which claims priority to Great Britain Patent Application No. 1013044.1, which was filed Aug. 3, 2010, all of which are incorporated by reference herein.

FIELD OF THE INVENTION

The present invention relates to rheometry apparatus, that is apparatus for rheological characterisation of a sample liquid. Certain embodiments are concerned in particular, although not exclusively, with micro-rheometers and apparatus for large scale high-throughput rheological characterisation of fluid samples using only very small volumes of complex fluids such as polymer solutions, DNA and protein solutions, synovial fluids, bloods, and other cellular solutions.

BACKGROUND TO THE INVENTION

A variety of rheometers are known for measuring rheological properties such as viscosity and elasticity of sample liquids. For example, US 2008/0134765 A1 discloses a micro-rheometer having micro-fabricated flow channels incorporating geometry changes to form constriction regions. The disclosed micro-rheometer also comprises an array of pressure sensors embedded within material forming one side of the flow channel. In this way, the pressure sensors are not in direct contact with fluid flowing within the flow channel. The thickness of material separating the pressure sensors from the flowing liquid is arranged such that the pressure sensors are able to provide measurements indicative of the pressure of the flowing fluid at the various locations of the sensors. The motivation for embedding (i.e. integrating) the pressure sensors in the body of material defining the flow channel in this way is to ensure that the flow of fluid within the channel is not disturbed or perturbed by the pressure sensors; a smooth, uninterrupted internal surface of the channel is provided. Although such apparatus is of use, it will be appreciated that disadvantages associated with the integrated pressure sensor arrangement are that the apparatus may be difficult and/or expensive to produce, once the arrangement has been manufactured there is no flexibility in where to locate the pressure sensors, and the separation of the pressure sensors from the flowing liquid by even a small thickness of material can reduce the accuracy of the pressure measurements obtained on the sample. Moreover, it only measures steady state viscosity of sample liquids.

SUMMARY OF THE INVENTION

It is an object of certain embodiments of the present invention to obviate, mitigate, or solve at least partly one or more of the problems associated with the prior art.

Certain embodiments aim to provide rheometry apparatus for large scale high-throughput rheological measurements. Certain embodiments aim to provide rheometry apparatus for dynamic measurements under oscillatory flow. Certain embodiments aim to provide rheometry apparatus that is simpler and cheaper to produce than previous arrangements. Certain embodiments aim to provide apparatus for use in rheometry which provides the user with flexibility in terms of the type and position of sensors to be used to measure characteristics of samples flowing in one or more flow channels. Certain embodiments aim to provide rheometry apparatus which can be used to obtain flow measurements from samples of liquids having very small volumes (i.e. 100 microliters and even smaller).

According to a first aspect of the present invention there is provided apparatus for use in rheometry, the apparatus comprising:

a block of substantially rigid material having an external surface and at least a first internal flow channel, the first internal flow channel being arranged inside the block and substantially in a plane and the block further comprising a plurality of holes, each hole communicating with the first internal flow channel at a respective position along the first internal flow channel and extending from the respective position to said external surface so as to provide access to the first internal flow channel from the external surface, the plurality of holes comprising a first hole communicating with a first said position, for connection to pumping means to drive fluid flow along said first internal flow channel, a second hole communicating with a second position and in which a sensor may be located to measure a property of fluid at the second position, and a third hole communicating with a third position and in which a sensor may be located to measure a property of fluid at the third position.

In certain embodiments the block is manufactured from a single body of material. However, in alternative embodiments the block is fabricated or assembled from separate components. For example, in certain embodiments the block formed from a rheochip of substantially rigid material having the internal flow channel or channels formed in it, and a separate block or body of material, which may be described as a service module for the rheochip, this separate block having the plurality of holes formed through it so as to communicate with the flow channel or channels in the rheochip when the rheochip and service module are secured together.

Thus, in contrast to prior art arrangements, sensors need not be embedded or integrated within the block of material (e.g. the microfluidic chip) in which the flow channel is defined. This enables the block (and hence the microrheometer as a whole) to be produced in a cost effective manner. Instead of integrating sensors into the block (e.g. microfluidic chip), those sensors can be located in the holes (which may also be referred to as access holes, chambers or apertures) provided in the block (e.g. in the service module). Thus, in certain embodiments there is flexibility in terms of the type and number of sensors to be used, and indeed their particular locations. The block (e.g. the service module) may be provided with a larger number of access holes providing access to a plurality of different positions along the internal flow channel so that pressure sensors or other sensors may be inserted at desired positions to monitor the fluid flowing in the internal channel.

In certain embodiments the plurality of holes comprises a fourth hole communicating with a fourth position for connection to reservoir means adapted to hold a reservoir of fluid. In certain embodiments, this fourth position is downstream of the third and second positions relative to the first position. In other words, the first position may be on one side of the second and third positions, and the fourth position may be on an opposite side of the second and third positions.

In certain embodiments the plurality of holes comprises a fifth hole via which fluid may be introduced into the flow channel. This fifth hole may also be used for extracting or expelling fluid from the flow channel. Alternatively, in other embodiments the plurality of holes comprises a sixth hole via which fluid can be extracted or expelled from the flow channel.

In certain embodiments, each of the plurality of holes (or at least a portion of each of the holes) extends in a direction substantially perpendicular to said plane.

In certain embodiments, each of said plurality of holes is threaded (i.e. it is provided with an internal screw thread for engagement by a corresponding external screw thread of a component to be screwed into the hole). This threaded arrangement facilitates connection of further components to the block to form a complete rheometer or rheometry system.

In certain embodiments, at least one of the plurality of holes comprises a first portion adjacent to the flow channel and a second portion adjacent to the external surface, the first portion providing a constriction between the flow channel and the second portion. In certain embodiments, each of the plurality of holes has this structure (i.e. incorporating a constriction).

It is particularly advantageous for the holes accommodating sensors to have this structure. The constriction enables flow in the flow channel to be substantially unaffected (i.e. undisturbed) by the sensor, which may be arranged in direct contact with fluid inside the hole but separated from the flow channel by the constriction.

In certain embodiments the constricted portion of the hole extends upwardly from the flow channel, that is in a direction generally perpendicular to the plane of the channel, and towards the external surface. In alternative embodiments the constricted portion of a hole may extend laterally, e.g. from a side of the flow channel.

In certain embodiments, the first portion is generally cylindrical, and this first portion may, advantageously, have a diameter smaller than a width of the flow channel at the position at which the hole is in communication with the flow channel. The use of a constricted first portion of such diameter further assists in the sensor arrangement being able to leave the flow within the flow channel unaffected.

In certain embodiments, the second portion of the or each hole is generally cylindrical, for example having a diameter substantially larger than the diameter of the first portion. In other words, the or each hole may widen out from the constricted portion connecting it to the flow channel, as one moves towards the external surface.

In certain embodiments a first portion of the hole which provides a constriction comprises a side channel extending from a side of the flow channel and substantially in the plane of the channel. In certain such embodiments the side channel has a width smaller than a width of the flow channel at the position where the side channel communicates with the flow channel. In general, the mouth of the side channel communicating with the flow channel should be made as small as fabrication techniques permit, whilst also enabling the fluid under test to be able to fill the side channel, so as to avoid affecting fluid flow in the flow channel that one is trying to monitor.

In certain embodiments, the side channel extends from the flow channel to a chamber portion of the respective hole (which may also be described as a side chamber), the chamber portion providing a chamber extending generally in the plane of the flow channel for containing a volume of fluid in communication, via the side channel, with the flow channel. A suitable sensor may then be arranged in communication (contact) with the fluid inside the side chamber, and this is easier to arrange than trying to arrange a sensor in direct communication with fluid in the side channel itself.

In certain embodiments, the second portion is provided with a screw thread for engagement by a correspondingly threaded portion of a pumping means, sensor housing, reservoir means, inlet or outlet connector, or other component or equipment required for constructing the rheometer or rheometry system as a whole.

In certain embodiments, the first portion is connected to the second portion by a shoulder against which an O ring may be compressed to form a seal, for example to seal a volume inside the hole and in communication with the flow channel.

In certain embodiments the block is substantially transparent to visible light, to facilitate micro-particle image velocimetry (PIV) and other rheo-optical measurements.

In certain embodiments the block is formed from PMMA or fused silica.

In certain embodiments the external surface is substantially flat.

In certain embodiments said block comprises a first block portion and a second block portion, the first internal flow channel being provided at an interface between the first and second block portion, said external surface being an external surface of the second block portion, and each said hole extending from said interface, through the second block portion, to said external surface. As will be appreciated, in certain embodiments one or more of the holes, in addition to extending from the interface through the second portion to the external surface, may also comprise a portion which extends generally along the interface. For example, in certain embodiments at least one of the holes comprises a side channel extending laterally from the respective flow channel, and this side channel may be provided at the interface between the first and second block portions. In embodiments incorporating an access hole which includes a side chamber or chamber portion in addition to the side channel, that chamber portion may also be provided at the interface. Typically, the relevant hole then comprises a further portion or portions which extend from the side channel or side chamber up to the external surface. In certain embodiments the first block portion may be the rheochip, and the second block portion may be the service module, as described above. In certain embodiments the junction between the first and second block portions may be visible, for example where the block is formed by clamping the first and second block portions together. In alternative embodiments, there may be no visible junction between the first and second block portions, for example where the block has unitary construction, or whether the first and second block portions were initially separate bodies of material, but have been attached together in such a way that the boundary between them is at least substantially invisible. In certain embodiment the first and second block portions may initially be separate, but may then be thermally bonded together.

In certain embodiments said first internal flow channel has been formed by forming a recess in a flat surface of the first block portion and attaching a flat surface of the second block portion to said flat surface of the first block portion.

In certain embodiments where one or more of the holes comprises a side channel, and optionally a side chamber or chamber portion, the side channel and/or side chamber may also have been formed by forming a respective recess or recesses in the flat surface of the first block portion. Advantageously, the same fabrication techniques used to form the recess which defines the flow channel may also be used to define the side channel and any side chamber. Advantageously, micro machining techniques and/or lithographic techniques may be used to define flow channels and side channels with very small widths.

In certain embodiments the first internal flow channel comprises a constricted portion (i.e. a constriction), which may be arranged to connect a first relatively unconstricted portion to a second relatively unconstricted portion.

In certain embodiments the second and third positions are located on either side of the constricted portion, whereas in alternative embodiments they are each located along the constricted portion.

In certain embodiments the first internal flow channel comprises a cruciform feature having four arms and the plurality of holes comprises four holes arranged for accommodating pressure sensors to measure the pressure of fluid flowing in each arm of the cruciform feature. Such apparatus may therefore be used to measure rheological properties under extensional flow around a stagnation point at the centre of the cruciform feature.

In certain embodiments the first internal flow channel comprises a plurality of flow-affecting features arranged in series such that pumping means connected to the first hole can drive fluid flow through the plurality of flow-affecting features simultaneously, the plurality of holes being arranged so as to permit sensors to be located to measure at least one property of fluid flow at, along, or across each flow-affecting feature. In alternative embodiments, the plurality of holes may be arranged so as to permit a limited access to just a limited number of the flow-affecting features.

In certain embodiments, the block comprises a network of internal flow channels arranged substantially in the plane, that network including the first internal flow channel. For example, the network of internal flow channels may be arranged to mimic a vascular system of a human or animal. In such embodiments, the first position may be arranged such that pumping means connected to the first hole can drive fluid flow through the network, the plurality of holes being arranged to permit location of sensors to measure at least one property of fluid flow at a plurality of positions over the network. In certain embodiments, a plurality of separate pumping means may be connected to a respective plurality of holes so as to drive fluid flow in the network from a plurality of positions.

In certain embodiments, the block comprises a plurality of separate internal flow channels, including said first internal flow channel, and a respective plurality of holes communicating with different positions along each separate flow channel, whereby the block may be used to measure at least one rheological property of a plurality of separate fluid samples simultaneously, each fluid sample being located in a respective one of the separate flow channels. Thus, such embodiments can be utilised to measure rheological properties of a large number of liquid samples simultaneously. Preferably, such embodiments may be combined with automated loading apparatus for automatically loading the different samples of liquid into the separate respective flow channels for testing.

In certain embodiments, each of the plurality of separate internal flow channels has the same geometry or configuration such that the same measurements may be performed on a plurality of different liquid samples simultaneously. In alternative embodiments, it will be appreciated that the separate flow channels may have different geometries or configurations such that different tests may be performed on different samples simultaneously.

In certain embodiments the apparatus further comprises pumping means connected to the first hole for driving fluid flow along the first flow channel. In certain embodiments the pumping means is operable to drive at least one of steady flow and oscillatory flow. In certain embodiments the pumping means may be controllable to provide both of these types of flow. In certain embodiments, the pumping means is a pressure pump, that is, pumping means adapted to drive the fluid flow by applying a controlled pressure to the fluid under test. This is in contrast to pumping means employed in alternative embodiments, where the pumping means comprises some actuating member or membrane which is displaced so as to set or determine the flow rate of fluid through the test channel. In certain embodiments, the pumping means is arranged to drive fluid flow through a plurality of flow channels simultaneously.

In certain embodiments, the pumping means is operable to generate suction to draw a sample of fluid into the flow channel via a hole other than the first hole. For example, a volume of fluid to be characterised may be loaded into a reservoir connected to one of the holes, and the pumping means may then be operated to generate suction to draw liquid from the reservoir to fill the flow channel and accessible volumes inside the other holes in communication with the flow channel (e.g. side-chambers in which sensors or sensing elements are located).

In certain embodiments the apparatus further comprises a pressure sensor (which may also be described as a pressure sensing element) arranged inside the second hole to measure the pressure of fluid within the second hole and in communication with the second position. In certain embodiments the pressure sensor is attached to a pressure sensor housing having an external screw thread engaged by a corresponding internal screw thread of the second hole. In such embodiments, the apparatus may further comprise sealing means arranged to prevent fluid flow from the first channel out of the second hole. In certain embodiments, this sealing means comprises an O ring arranged to form a seal between a surface of the pressure sensor housing and an internal surface of the second hole. In certain embodiments, the O ring is arranged to be compressed between an end surface of the pressure sensor housing and a shoulder of the second hole when the housing is screwed into the second hole. In such arrangements, the pressure sensor or sensing element may be arranged so as to be in direct contact with fluid sealed inside the second hole by the O ring.

Similarly, in certain embodiments the apparatus may further comprise a pressure sensor arranged inside the third hole to measure the pressure of fluid within the third hole and in communication with the third position.

It will be appreciated that sensors for measuring other properties of fluid flowing in the flow channel may be incorporated in addition or as an alternative to the above-mentioned pressure sensors. These additional or alternative sensors may, advantageously, be connected to housings adapted for releasable attachment and sealing in the holes in any of the manners described above.

In certain embodiments, the first flow channel has a volume less than 100 microliters. In certain other embodiments, the first flow channel has a volume even smaller.

In certain embodiments, the apparatus further comprises reservoir means connected to the fourth hole and arranged to hold a volume of liquid in communication with the first flow channel. In such embodiments, the reservoir may be arranged such that the held volume of liquid has a surface exposed to atmosphere.

In certain embodiments the apparatus further comprises an automated loading system for loading fluid into the or each fluid channel.

Another aspect of the present invention provides rheometry apparatus comprising:

a block of substantially rigid material having an external surface and at least a first internal flow channel, the first internal flow channel being arranged inside the block and substantially in a plane and the block further comprising a plurality of access holes, each hole communicating with the flow channel at a respective position along the flow channel and extending from the respective position to said external surface so as to provide access to the flow channel from the external surface such that pumping means and sensing means may be selectively connected to the access holes to drive fluid flow along the channel and measure one or more properties of fluid flowing along the channel.

Advantageously, each access hole may be provided with an internal screw thread to facilitate connection of sensors, pumping means etc.

According to another aspect of the present invention there is provided a method of manufacturing a rheometer, the method comprising:
  providing a first body of substantially rigid material having a flat surface;
  forming at least one channel (recess, groove) in said flat surface;
  providing a second body of substantially rigid material having a flat surface, for mating with the flat surface of the first body, and an external surface;
  forming a plurality of holes through the second body, from the flat surface to the external surface, at selected positions;
  mating said flat surfaces together such that at least a first internal flow channel is defined by said at least one channel in the flat surface of the first body and the flat surface of the second body, and such that each hole communicates with the first internal flow channel at a respective position along the first internal flow channel so as to provide access to the first internal flow channel from said external surface, whereby pumping means and sensing means may be connected to the holes to drive fluid flow along the first internal flow channel and measure one or more properties of fluid flowing along the first internal flow channel.

According to another aspect of the present invention there is provided a method of manufacturing a rheometer, the method comprising: providing a first body of substantially rigid material having a flat surface; forming a channel, a side channel extending from a side of the channel, and optionally a side chamber at an end of the side channel, in said flat surface; providing a second body of substantially rigid material having a flat surface, for mating with the flat surface of the first body, and an external surface; forming a hole through the second body, from the flat surface to the external surface; mating said flat surfaces together such that an internal flow channel is defined by said channel and the flat surface of the second body, and such that said hole communicates with either the side channel or the side chamber, whereby sensing means may be connected to said hole to measure a property of fluid flowing along the flow channel.

Advantageously, the channel and side channel may be formed at the same time, using the same fabrication techniques, for example micro machining and/or lithography. Thus, the side channel width can be made very small, so that its presence does not affect fluid flow in the flow channel yet enables monitoring or measurement of a fluid property in the flow channel. In certain embodiments, less accurate techniques may be used to form the hole through the second body, such as conventional drilling or other machining techniques. Advantageously, in embodiments incorporating a side chamber at an end of the side channel opposite an end of the side channel communicating with the flow channel, the side chamber can be made relatively large, i.e. having at least one dimension much larger than the width of the side channel, to facilitate alignment between the hole in the second body and the side chamber. Thus, whilst the hole through the second body may have been manufactured using techniques less precise than those used to form the side channel, the second body only has to be aligned with sufficient accuracy to place the hole in communication with the side chamber, and not the finer side channel. A suitable sensor may then be located in the hole in the second body, that sensor being in communication with the side chamber, and hence also in communication, via the side channel, with the fluid flowing in the flow channel.

In certain embodiments, the method further comprises providing each hole with a respective internal screw thread.

Certain embodiments further comprise bonding the flat surfaces together. In such embodiments, the first and second bodies may each be formed from a thermoplastic material, and the bonding may comprise thermal bonding.

In certain embodiments, the method further comprises positioning a pressure sensing element (which may also be described as a pressure sensor) inside at least one of the holes. In such methods, the method may also comprise providing a constriction between the pressure sensing element and the first flow channel. This may be achieved, advantageously, by arranging for the hole to accommodate the sensor being manufactured such that it has a relatively narrow opening onto the flow channel, and then a wider portion adjacent the external surface for accommodating the sensor. The method may then further comprise forming a seal to prevent fluid flowing out of the hole containing the pressure sensor to the external surface.

Advantageously, arranging a sensor inside a sealed volume or side chamber, separated from the flow channel by a constriction, such as a small diameter mouth, a property of fluid flow within the channel can be accurately measured without disturbing flow and without requiring expensive and inflexible integration of a sensor or sensors within the first or second bodies during manufacture.

BRIEF DESCRIPTION OF DRAWINGS

Embodiments of the present invention will now be described with reference to the accompanying drawings, of which.

DETAILED DESCRIPTION OF EMBODIMENTS OF THE INVENTION

Figure 1:
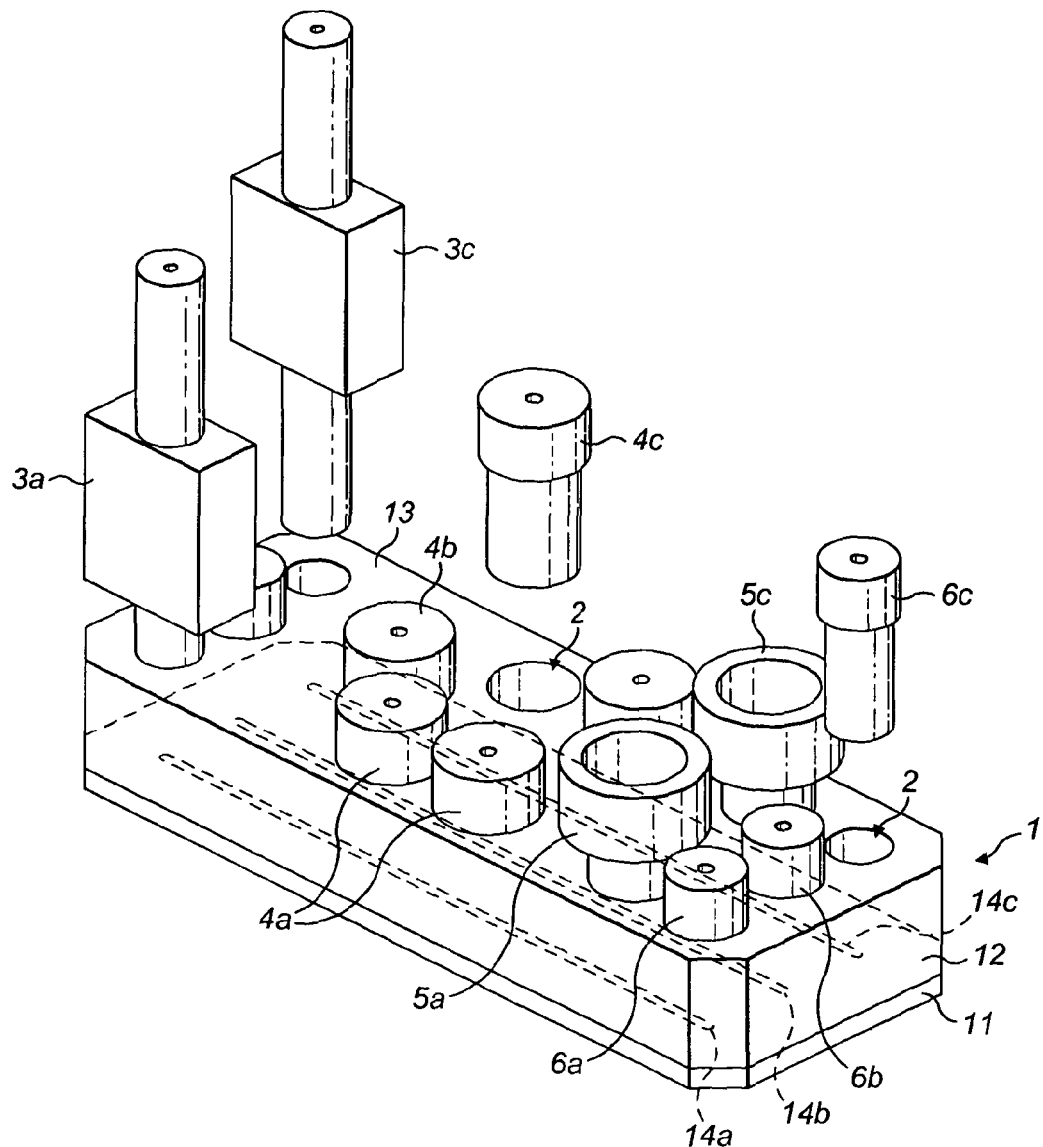
FIG. 1 is a perspective view of an assembly of the key components of a rheochip-based micro-rheometer for larger scale, high throughput rheometrical characterisation of complex fluids embodying the invention.

Referring now to FIG. 1, a rheometer (which may also be described as rheometry apparatus and/or a rheometry system) embodying the present invention comprises a block 1 of substantially rigid and transparent material formed by attaching a first block portion 11 to a second block portion 12. The assembled block 1 comprises three separate and co-planar micro flow channels 14a, 14b, and 14c. These three flow channels are defined at the interface between flat mating surfaces of the first block portion 11 and second block portion 12. The block 1 also comprises a plurality of access holes 2, each of which is arranged to communicate with one of the internal flow channels at a respective position along that channel's length and to extend from that position upwards to a substantially flat external surface 13 of the block 1. Thus, each hole or aperture 2 provides access to one of the internal flow channels so that pumping means, sensors etc can be attached to the block 1 and generate a measure characteristics of fluid flow in the channels 14a-c. In this first embodiment, pumping means 3a is connected to a first hole communicating with the flow channel 14a so as to drive fluid flow along that channel. Pressure sensors are located in second and third holes communicating with flow channel 14a, those pressure sensors each being mounted on pressure sensor housings 4a. A micro reservoir 5a is attached to a fourth hole communicating with the channel 14a, and an inlet/outlet connector 6a is inserted in a fifth hole. With regard to the second internal channel 14b, a sensor housing 4b is inserted in one of the communicating access holes, and an inlet/outlet connector 6b is inserted in a further access hole.

With regard to the third micro channel 14c, a further pumping means 3c is shown ready for insertion in a corresponding access hole, as is a sensor housing 4c. A reservoir 5c has already been positioned in one of the access holes, and an inlet/outlet connector 6c is shown ready for insertion in a further access hole 2.

It will be appreciated that the illustrated arrangement provides the advantage that there is flexibility in the particular configuration of sensor types and positions, and indeed the pumping means. Different sensors may be attached to (i.e. "plugged in" to) the block 1 to access the embedded micro channels and perform a variety of rheological measurements. In the illustrated arrangement, pumping means 3a and 3c may be independently controlled to perform separate rheological measurements simultaneously on a first sample accommodated within channel 14a, and a further sample accommodated within channel 14c.

Figure 2:
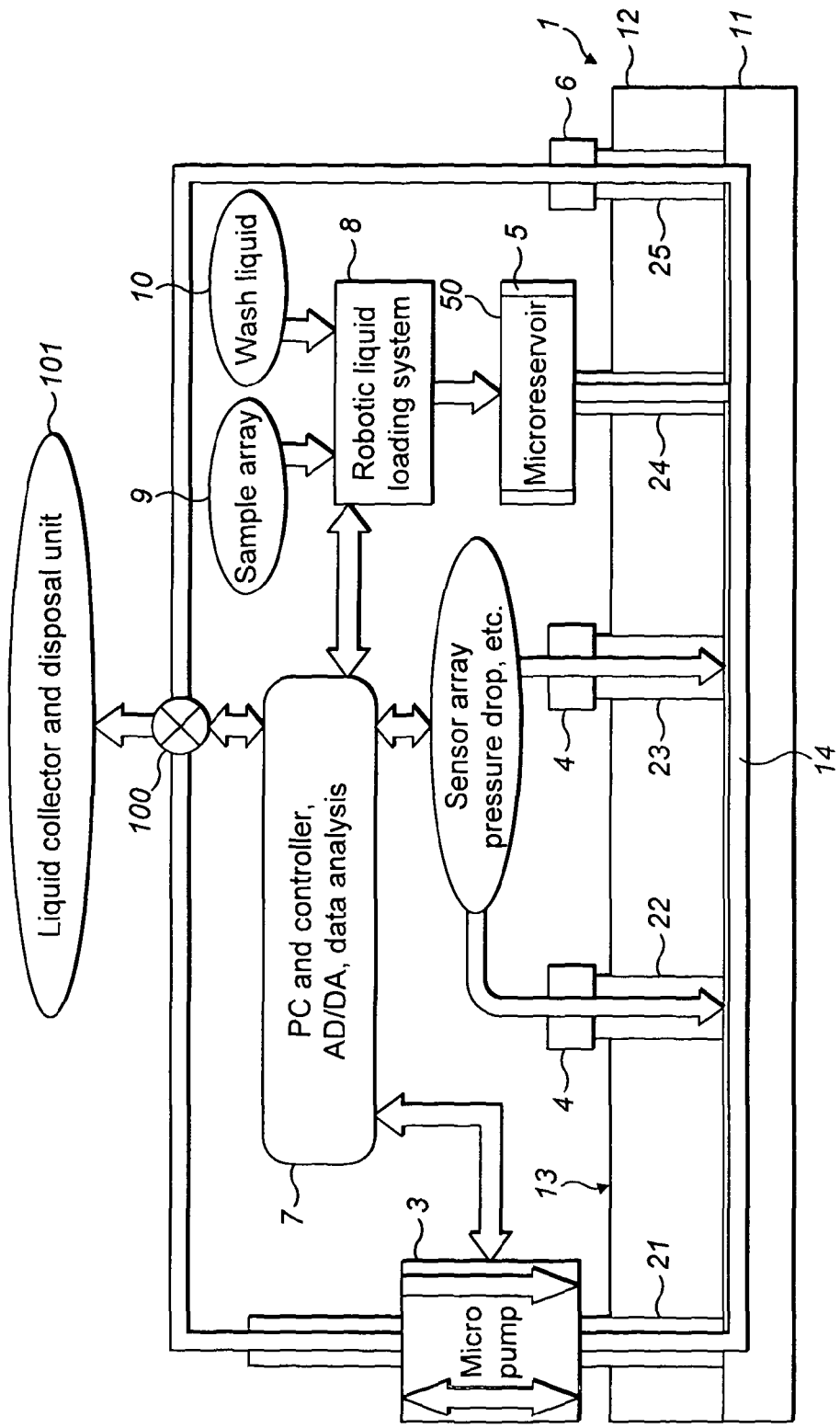
FIG. 2 is a schematic representation of components of a rheometer embodying the invention.

Referring now to FIG. 2, this illustrates another embodiment of the invention. Again, the block 1 comprises a lower portion 11 and an upper portion 12, that upper portion 12 having a substantially flat external surface 13. A flow channel 14, which is substantially in a single plane, is defined substantially at the interface between mating flat surfaces of the upper and lower blocks 11, 12. A micro pump 3 is arranged to generate either steady flow of fluid at a desired flow rate within the channel 14 or oscillatory flow at a desired frequency and amplitude. The steady flow rate, frequency, and amplitude are each adjustable by means of suitable control of the micro pump 3 by the control means 7 which comprises a PC and controller, AD/DA converters and data analysis means. The micro pump 3 is connected to a first hole 21 in the upper block 12. Pressure sensors mounted in housings 4 are connected to holes 22 and 23. Although not shown in the figure, the pressure sensing elements are located at or proximate the lower ends of these housings 4 such that they are in direct contact with volumes of test fluid located just inside the respective holes 22 and 23, adjacent the flow channel 14. These pressure sensors are also connected to the control means 7. A micro reservoir 5 adapted to hold a volume of liquid to be characterised is attached to a fourth hole 24, the contained liquid having a surface 50 exposed to atmospheric pressure in this example. The system further comprises an inlet/outlet connector 6 connected to a fifth hole 25. The micro pump 3 and inlet/outlet connector 6 are each connected to a valve 100, which is also connected to a liquid collector and disposal unit 101. The valve 100 is controlled by the control means 7. The system further comprises a robotic liquid loading system 8 which is adapted to access an array of samples (i.e. small volumes of liquid) 9 and a reservoir of wash liquid 10 for cleaning and purging the system after each sample measurement. In order to perform a measurement on a particular sample, the robotic liquid loading system accesses the sample from the sample array 9, places the sample in the micro reservoir 5, and then the micro pump is controlled to generate suction to draw sample liquid down from the micro reservoir into the flow channel 14 and also to fill the side-volumes inside the pressure sensor holes 22 and 23. After loading, the micro pump is then controlled to generate the desired flow and the pressure sensors are used to obtain measurements of fluid pressure at the two positions along the flow channel 14 with which the holes 22 and 23 are in communication.

Figure 2A:
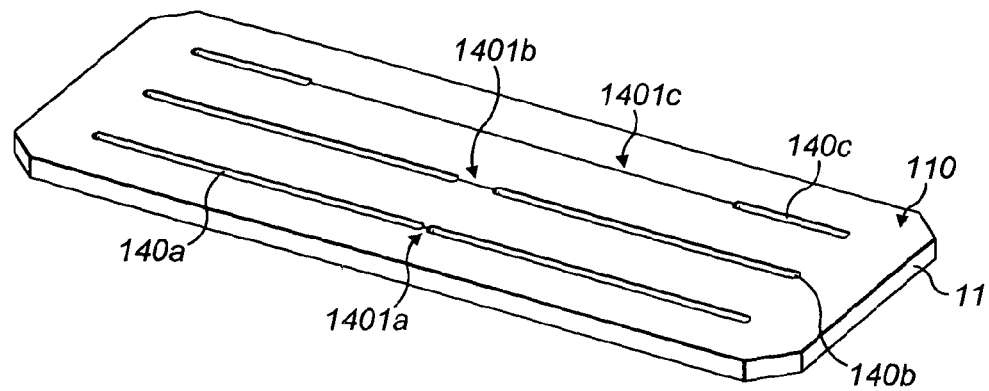
FIGS. 2a-2i illustrate components of rheometry apparatus embodying the invention.

Referring now to FIGS. 2a-2i, these show various components of certain embodiments of the invention. FIG. 2a shows a rheo-chip with micro-fabricated flow channels in various designs. This rheo-chip is a first body of rigid material 11 with a plurality of channels (which may also be referred to as grooves or recesses) 140a-140c formed in a substantially flat surface 110. Each of these channels includes a respective constriction 1401a-1401c.

Figure 2B:
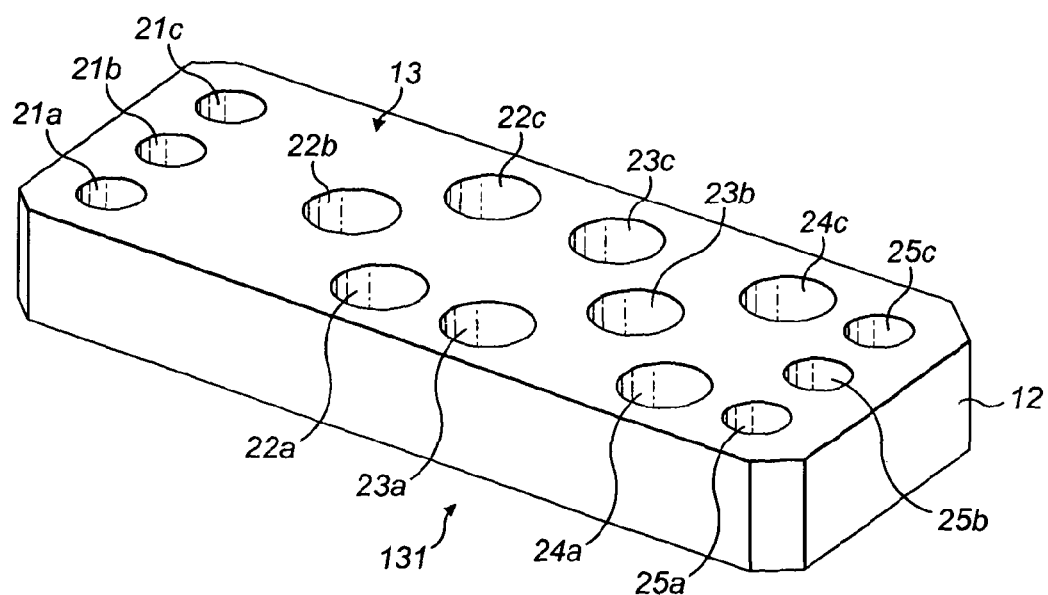

FIG. 2b illustrates an upper body 12 having a flat surface 131 for mating with the flat surface 110 of the first body 11 shown in FIG. 2a. This body or block portion may also be described as a service module for rheo-chips to control flow and temperature, and integrated with rheo-chip, micro pump, micro sensor probes (pressure, temperature, pH, oxygen, carbon dioxide, etc.), micro-reservoir, valves, inlet and outlet connectors etc. This second portion 12 comprises a plurality of holes, each extending through the second body 12 from the lower flat surface 131 to the upper, external surface 13. These holes include respective first holes 21a-21c, respective second holes 22a-22c, respective third holes 23a-23c, respective fourth holes 24a-24c, and respective fifth holes 25a-25c. Each hole is positioned such that when the upper portion 12 is attached to the lower portion 11, each hole provides access to a respective one of the plurality of internal flow channels defined in the interface between the portions 11 and 12.

Figure 2C:
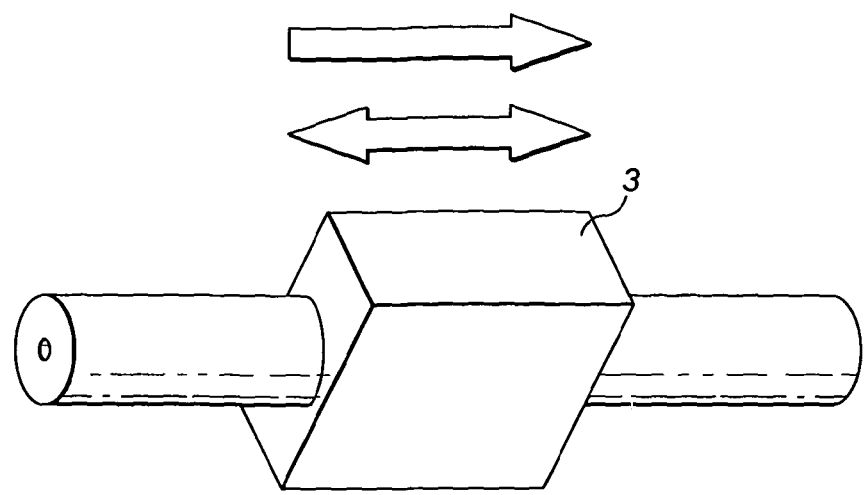

FIG. 2c illustrates a micro pump 3 operable to generate either steady flow in a given flow rate or oscillatory flow in a given frequency and amplitude.

Figure 2D:
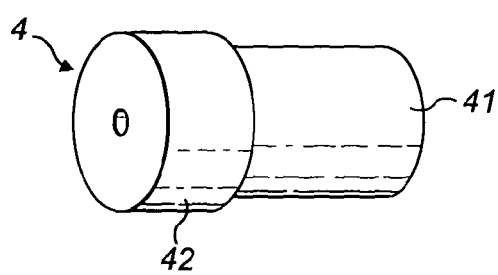

FIG. 2d illustrates a sensor housing of a geometry which may be used to carry a variety of sensors or sensing elements in embodiments of the invention. The housing 4 may therefore be arranged to house or carry a variety of micro sensor probes, such as pressure sensors, temperature sensors, pH sensors, etc. The sensor housing comprises a first generally cylindrical portion 41 and a second generally cylindrical portion 42. The first cylindrical portion 41 has a smaller diameter than the second cylindrical portion 42, and is arranged for insertion in any one of the second or third holes 22, 23 in the surface module 12. Although not shown in the figure, this first cylindrical portion 41 may be threaded (i.e. provided with an external screw thread) for engagement by a corresponding internal screw thread provided in the second and third holes 22, 23. Although not shown in the figure, the sensor carried by the sensor housing 4 may be located at or proximate the end of the first portion 41 furthest from the second portion 42. Thus, when the sensor housing is located into the corresponding hole 22 or 23, the sensor is positioned close to the respective flow channel.

Figure 2E:
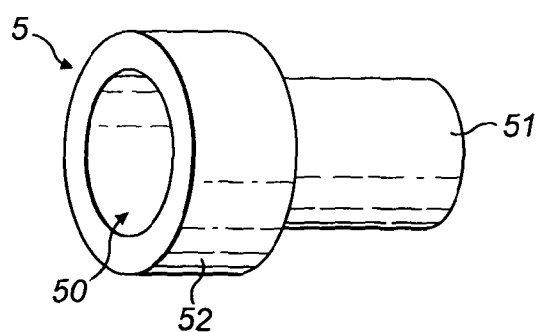

FIG. 2e illustrates a sample micro reservoir which may be used in embodiments of the invention. The micro reservoir 5 comprises an internal cavity 50 for holding a quantity of liquid sample to be tested, and has a first cylindrical portion 51 (which may be provided with an external screw thread) for location in one of the fourth holes 24a-24c of the service module, and a second cylindrical portion 52 of wider diameter.

Figure 2F:
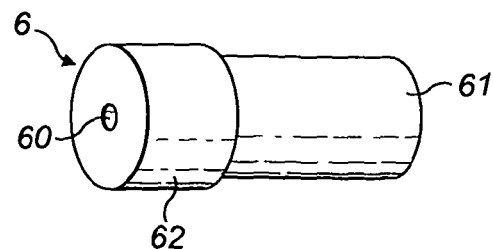
Figure 2G:
Figure 2H:
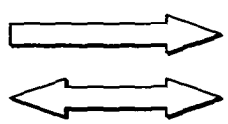
Figure 2I:
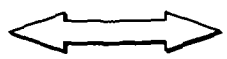

FIG. 2f illustrates an inlet/outlet connector which may be used in embodiments of the invention. Again, the connector comprises a first cylindrical portion 61 for insertion in any one of holes 25 in the service module, and a second cylindrical portion 62 of increased diameter. The connector 6 also comprises a bore 60 providing a fluid conduit completely through the connector along its longitudinal axis. FIGS. 2g-2i illustrate further components of the system shown in FIG. 2.

Figure 3:
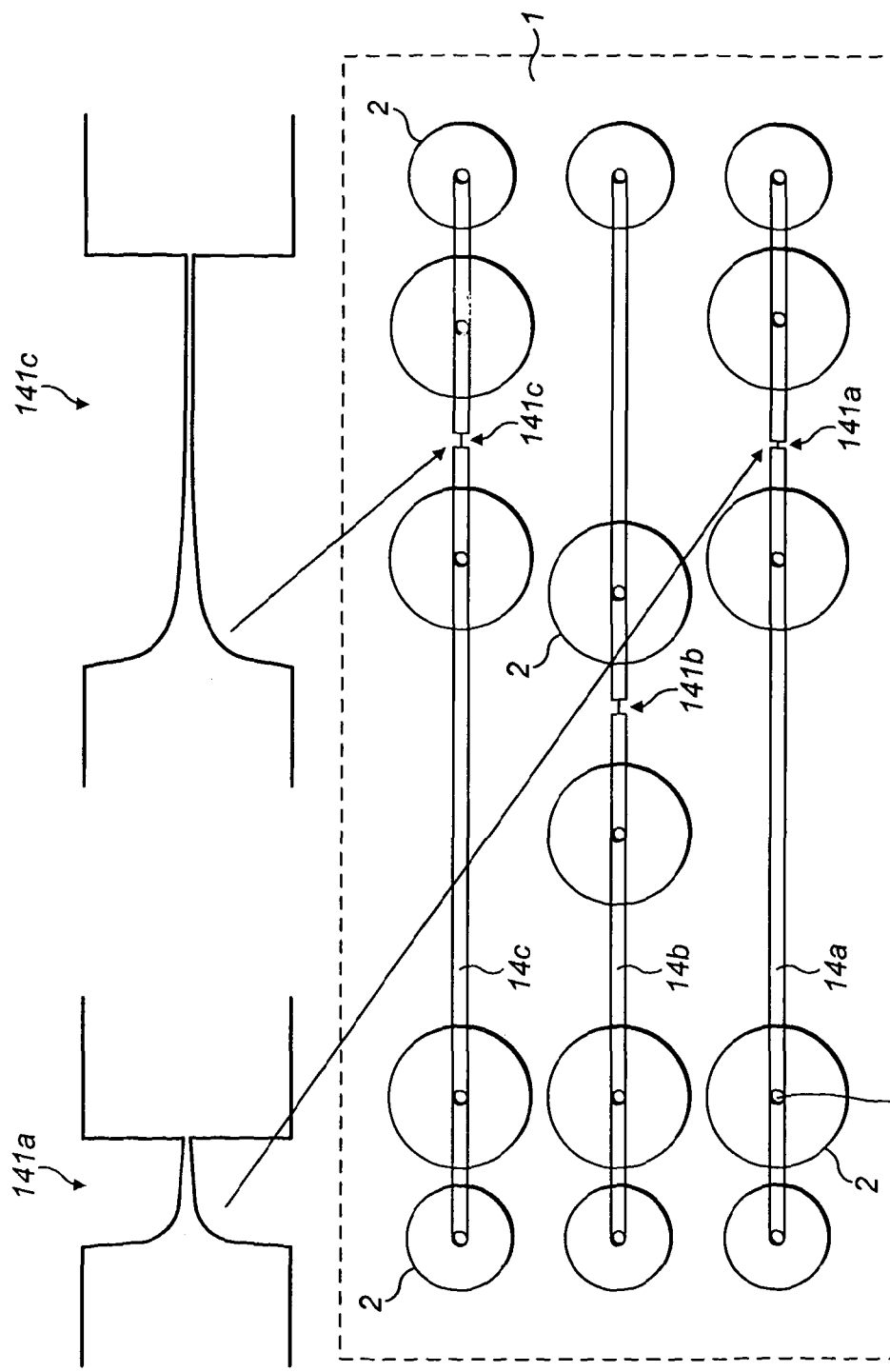
FIG. 3 illustrates rheometry apparatus in accordance with another embodiment of the invention.

Referring now to FIG. 3, this illustrates an other embodiment of the invention. In this embodiment, the rigid block 1 is provided with three separate internal flow channels 14a, 14b, and 14c and a plurality of access holes 2 providing access to the internal channels from the upper external surface of the block 1. Each access hole 2 has an upper portion adjacent the external surface and having a relatively larger diameter, and a lower portion having a relatively small diameter, providing a constriction between the relatively larger diameter portion and the respective internal channel. In this embodiment, the diameter of the mouth 20 provided by each lower hole portion to connect the hole to the respective flow channel is smaller than the width of the flow channel at the relevant position.

In the embodiment of FIG. 3, each of the flow channels 14a-14c is provided with a respective constriction or constricted portion 141a-141c. Two of these constricted portions 141a and 141c are shown in greater detail at the top of the figure. Pressure sensors may be arranged in holes located on either side of these constrictions to measure pressure drops across the constrictions when fluid flow is driven along the respective channels by means of pumping means connected to further holes 2.

It will be appreciated that the embodiment of FIG. 3 may comprise a block 1 formed from a rheochip and a corresponding service module. The embodiment of FIG. 3 thus can be considered as representing an example of rheochip design to simultaneously measure shear and extensional viscosity in various sizes of micro channel.

In FIG. 3, the plurality of access holes 2 are shown, but not all of them are labelled so as not to reduce the clarity of the figure. However, it will be appreciated that each access hole has a circular opening at the upper, external surface of the block 1. In the figure, the access holes at the extremities of the three channels are holes for inlet/outlet and pump connections. The larger holes just to the right of the smaller holes at the left hand extremity of each channel are holes for connection to reservoirs. The pairs of holes immediately next to, and surrounding each constriction are holes in which sensors may be located.

Figure 4:
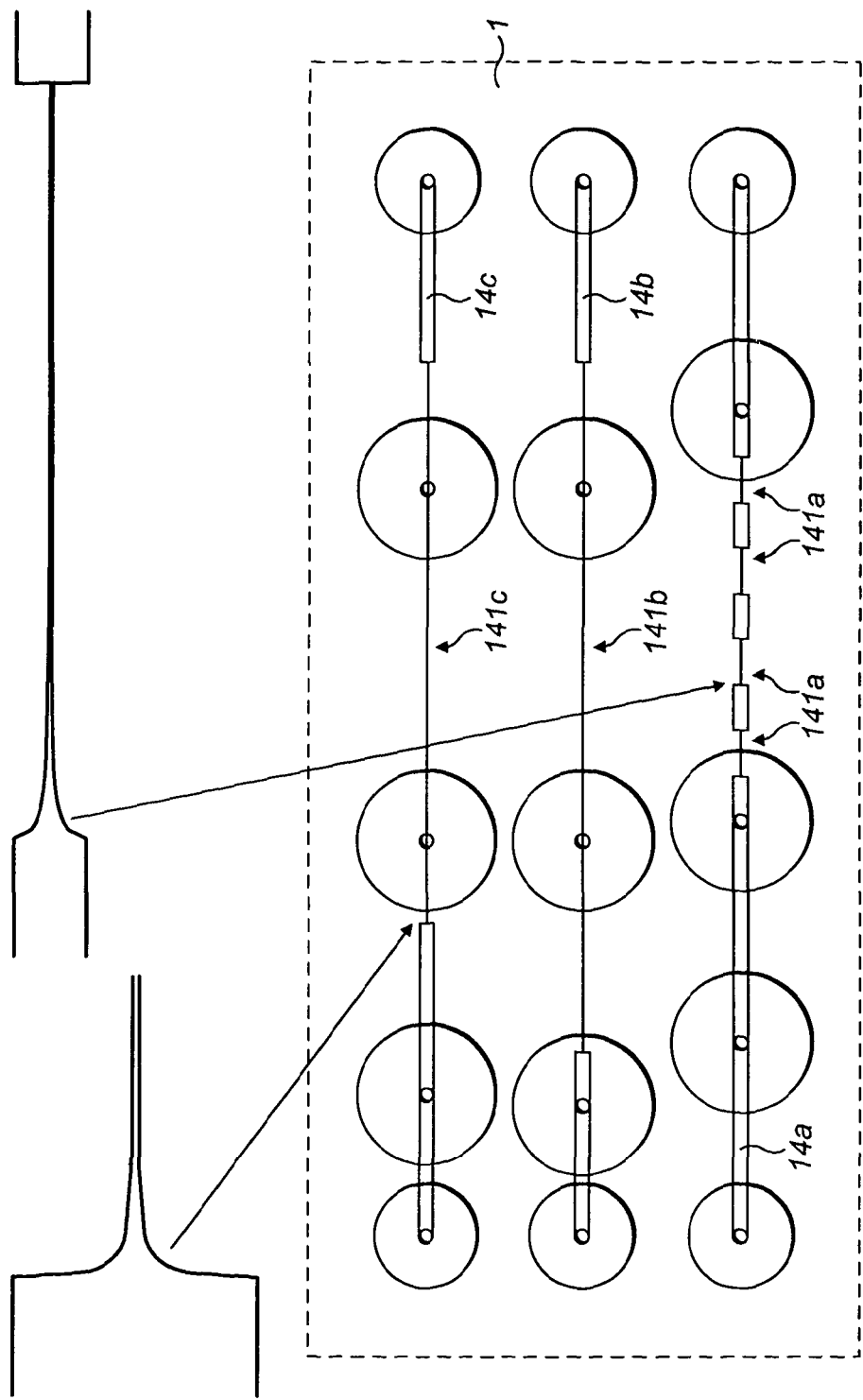
FIG. 4 illustrates further rheometry apparatus embodying the invention.

Referring now to FIG. 4, this illustrates yet another embodiment. Here, three separate flow channels 14a-14c are again provided internally in a block 1. The first flow channel 14a is provided with a series of constrictions or constricting features 141a and a plurality of access holes to this first channel 14a are provided to enable the connection of pumping means to drive fluid flow in this channel and measure pressure at a plurality of positions. These positions include positions on either side of the sequence of constrictions 141a. For channel 14b, a relatively long constricted portion 141b is provided, and access holes are provided to enable pressure sensors to be located so as to measure pressure at two locations along the constricted portion itself. Similarly, the third channel 141c is provided with a plurality of access holes to enable pumping means to drive flow along the channel and to enable pressure to be measured at two positions along the constricted portion 141c, between relatively unconstricted portions.

Figure 5:
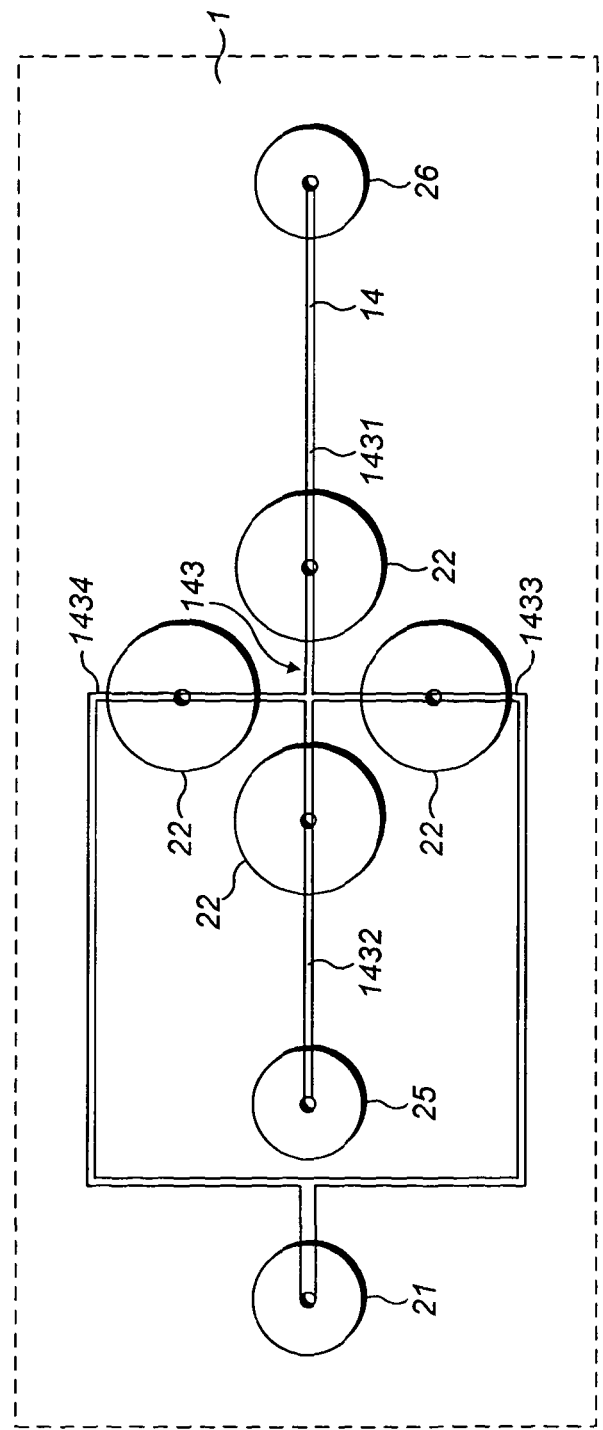
FIG. 5 illustrates yet another embodiment of the invention (an example of rheochip design to measure transient and steady-state viscosity)

Referring now to FIG. 5, this illustrates another embodiment which may be described as a rheo-chip designed to measure transient and steady state viscosity. The flow channel 14 defined internally within the block 1 comprises a cruciform feature or cross 143 having four arms 1431-1434. A plurality of access holes 2 are provided, four of these holes being arranged so as to enable pressure difference measurements to be made between each of the four arms of the cruciform feature 143. Pumping means may be connected to access inlet holes so as to drive fluid flow in the channel 14. In this embodiment hole 21 is an inlet hole for connection to a pump or other pumping means for driving fluid flow in the channel 14. Access holes 22 are the holes in which pressure sensors are to be located. Access hole 25 is an outlet hole, as is hole 26.

Figure 6:
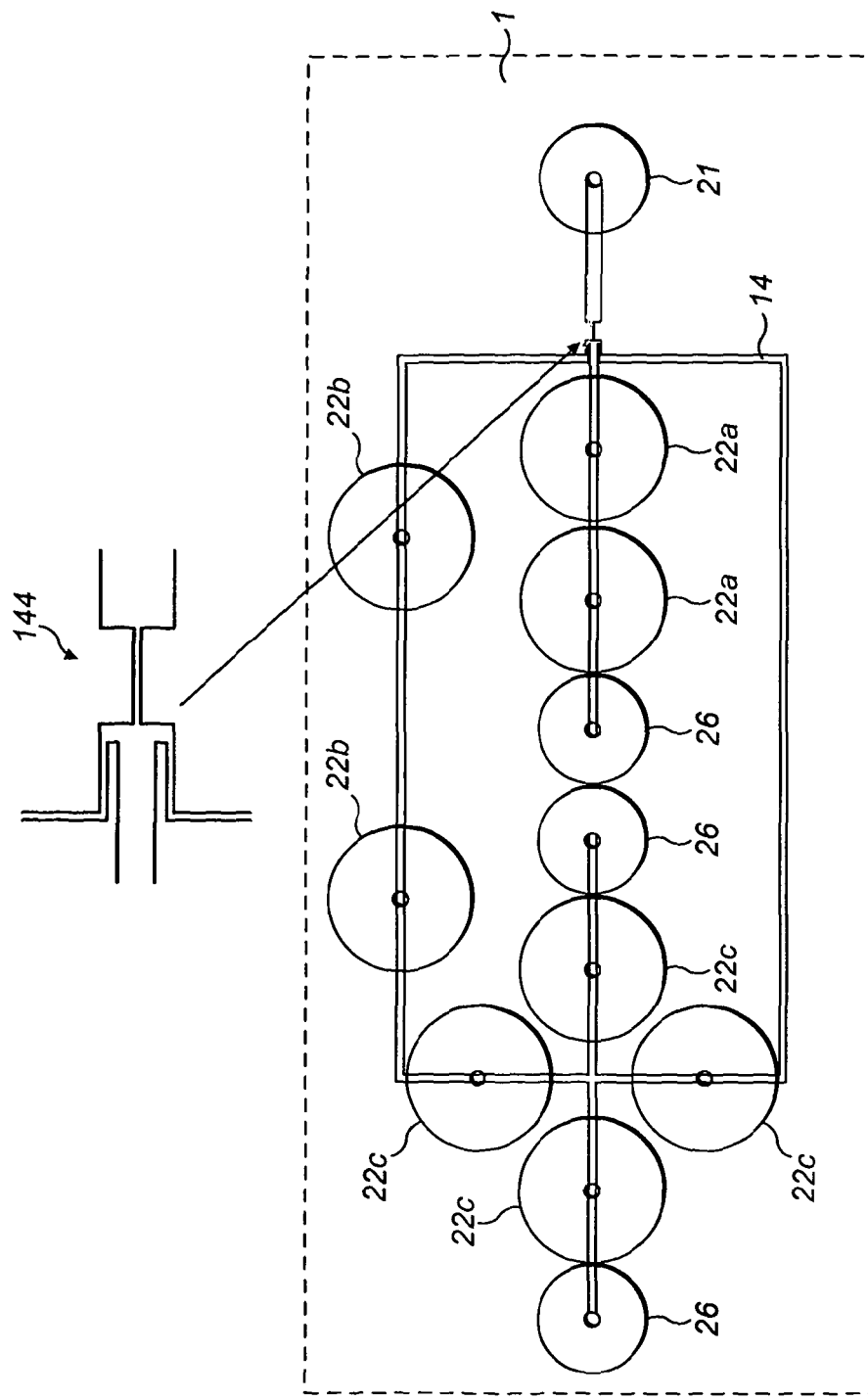
FIG. 6 illustrates rheometry apparatus in accordance with another embodiment of the invention.

Referring now to FIG. 6, this shows another embodiment of the invention. Here the block 1 is provided with a flow channel arrangement comprising a plurality of features 143, 144. Feature 143 is a cross, the centre of which typically forms a stagnation point. Feature 144 is for separation of cellular elements from plasma. It will be appreciated that the arrangement shown in FIG. 6 is an example of a rheochip design to separate cellular elements from plasma and to measure their shear and extensional viscosity. Hole 21 is an inlet and pump connection hole. Holes 26 (the rest of the smaller holes) are outlet holes. Holes 22a are pressure sensor holes for accommodating pressure sensors to measure rheological properties of blood with high concentration of cellular elements. Holes 22b are pressure sensor holes for locating pressure sensors to measure rheological properties of plasma under shear flow. Holes 22c are pressure sensor holes for measuring rheological properties of plasma under extensional flow.

Figure 7:
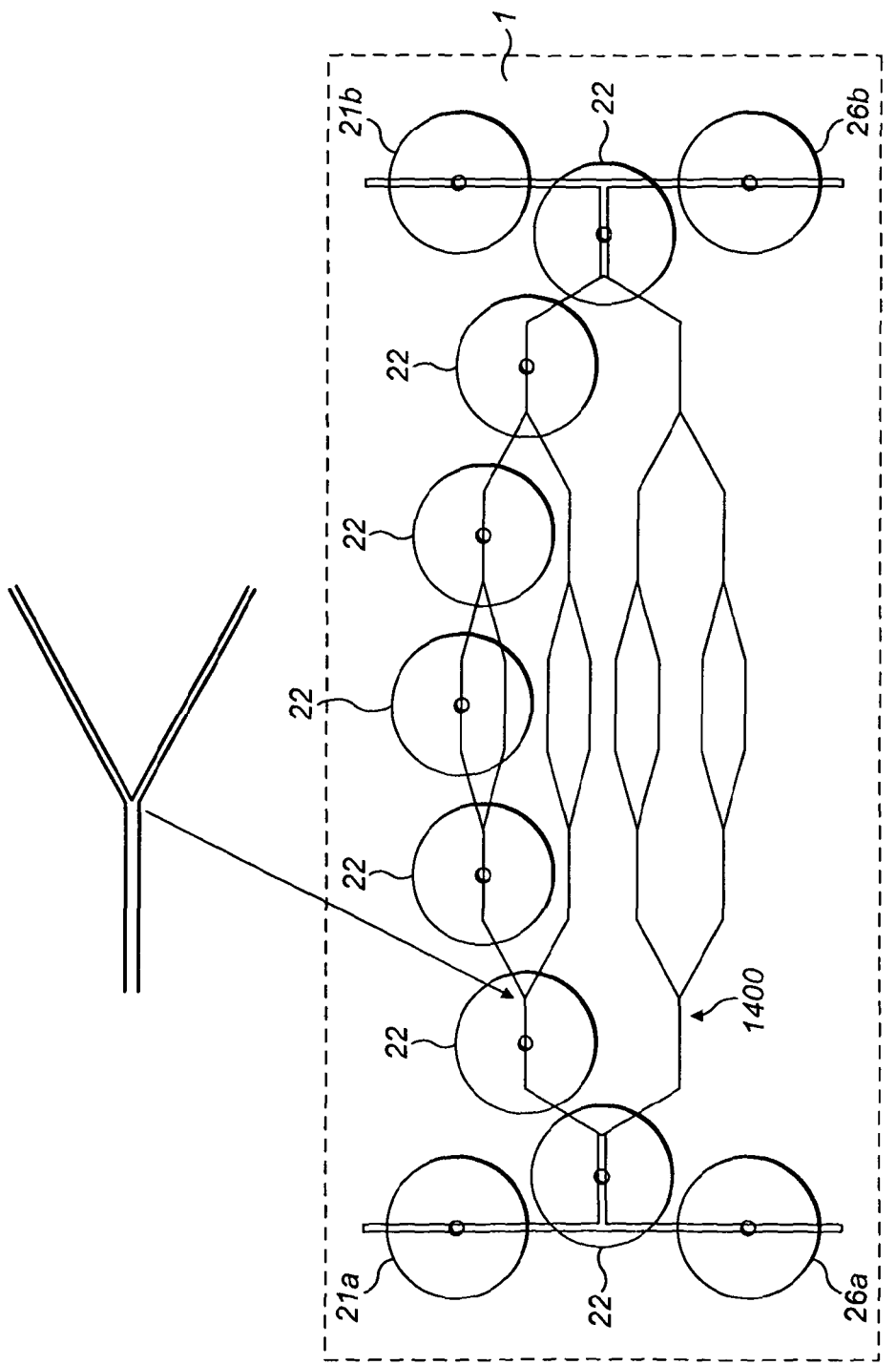
FIG. 7 illustrates yet another embodiment of the invention (an example of rheochip design to mimic haemodynamics in microcirculation)

Referring now to FIG. 7, this illustrates yet another embodiment of the invention. Here the block 1 is provided with a substantially planar internal network 1400 of flow channels having a branching configuration to mimic a vascular system. A plurality of holes are provided in the block to provide access for pressure measurement at a plurality of different positions across the network. Further holes are provided to enable pumping means to be connected to drive flow through the branching network. In particular, hole 21a is an inlet and push-pump hole, that is a hole to which a pump is to be attached to drive or push fluid through the branching network of channels 1400. Hole 26a is an outlet hole. Hole 21b is an outlet and pulling-pump hole, that is a hole to which pumping means may be connected so as to generate suction to pull or draw fluid through the network of channels. Hole 26b is another outlet hole. Holes 22 are holes for the location of pressure sensors to measure the pressure at various points over the network, and to measure pressure differences between different points in the network.

Figure 8:
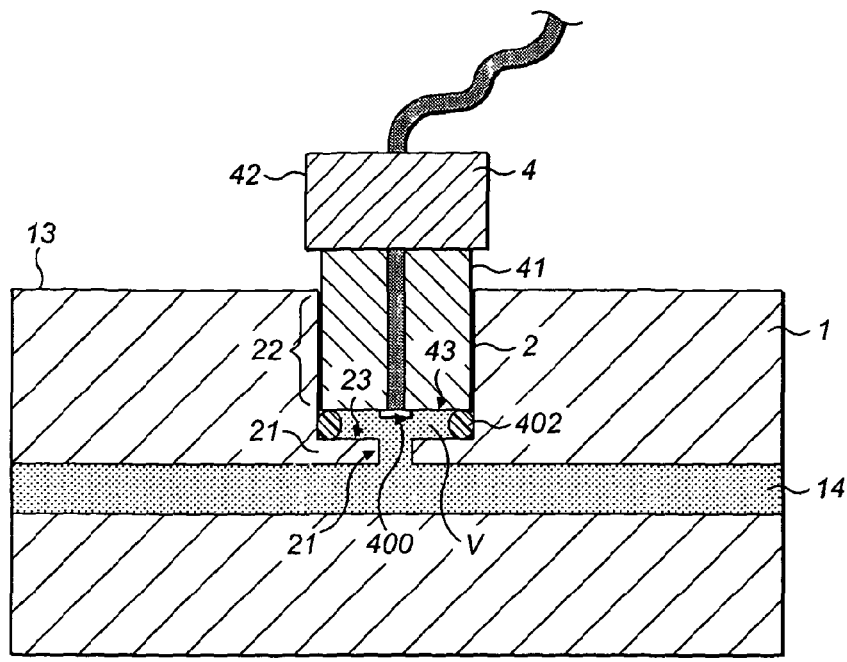
FIGS. 8-10 illustrate further details of certain embodiments of the invention.

Referring now to FIG. 8, this illustrates the attachment of a sensor housing 42 to a block 1 in an embodiment of the invention. A first cylindrical portion 41 of the housing 4 is located within an upper portion 22 of the hole 2. This first portion 41 has a flat end surface 43, at which a pressure sensor 400 is located. The housing portion 41 and hole portion 22 are provided with external and internal screw threads respectively, such that the housing 41 can be screwed into the hole 2 so as to compress an O ring 402 between the flat end surface 43 and a flat shoulder 23 connecting the second hole portion 22 to a first hole portion 21. Portion 21 has much reduced diameter, forming a constriction.

As mentioned above, the pressure sensing element 400 is located at the end surface 43 of the housing in this example. It will be appreciated that in alternative embodiments the location of the pressure sensor 400 may be different. For example, it may be located close to or just inside the end surface of the housing. However, these embodiments have in common the fact that the pressure sensor 400 is located so as to be in direct contact with the small volume V of fluid inside the access hole 2 (i.e. inside the chamber defined between the sensor housing 4, the sealing means 402, and the hole 2) which is itself in fluid communication (via constricted portion 21) with the fluid flowing in the channel 14. In certain embodiments, the constriction or first portion 21 of the hole 2 has a diameter of approximately 0.3 mm, and the width of the channel 14 with which the constriction is in communication is 0.3 mm. By arranging the diameter of the constriction 21 to be substantially smaller than the width of the channel at the connecting point in this way, the flow of fluid in the channel 14 is substantially unaffected (i.e. undisturbed or unperturbed) by the mouth of the connecting portion 21 in the wall of the channel 14, and the pressure of the volume of fluid V inside the access hole 2 is substantially the same as the pressure of the fluid at the point just next to the constriction 21. It will be appreciated that a variety of materials may be used for the O ring 402, for example rubber. Also, it will be appreciated that a variety of other forms of sealing means may be employed to form a suitable seal between a sensor housing and the access hole 2 into which the housing, or part of it, is inserted.

Figure 9:
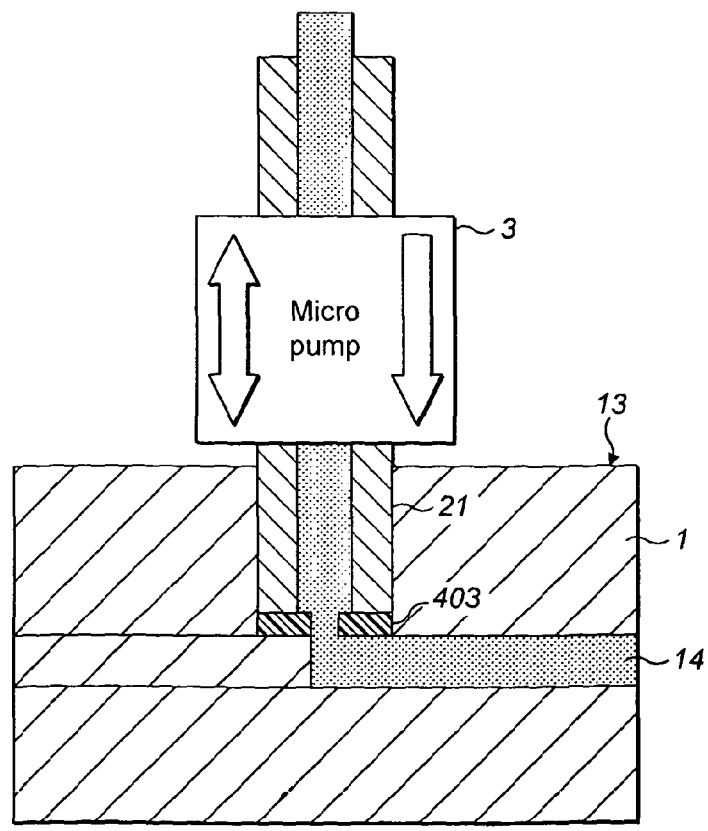

Referring now to FIG. 9, this shows details of a micro pump assembly (pumping means) connected to an access hole 21 of a rheometer block 1 in an embodiment of the invention. The micro pump assembly 3 comprises a main body housing the pump actuating means which is controllable to drive either steady flow or oscillatory fluid flow. The assembly 3 includes connecting portions, each of which is substantially cylindrical, and a lower one of which is inserted into the access hole 21. Although not shown in the figure, in certain embodiments the connecting portion of the pump assembly 3 is provided with an external screw thread which is engaged by a corresponding internal screw thread provided inside the access hole 21 (which may also be described as a threaded bore or comprising a threaded bore). Beneath the lower connecting means of the pump assembly 3 there is provided sealing means in the form of a fringeless hard rubber seal 403, i.e. a hard rubber seal having no edges. This rubber seal has a central hole, aperture, or bore with which an outlet conduit or bore of the pump assembly 3 is in fluid communication with the flow channel 14.

Figure 10:
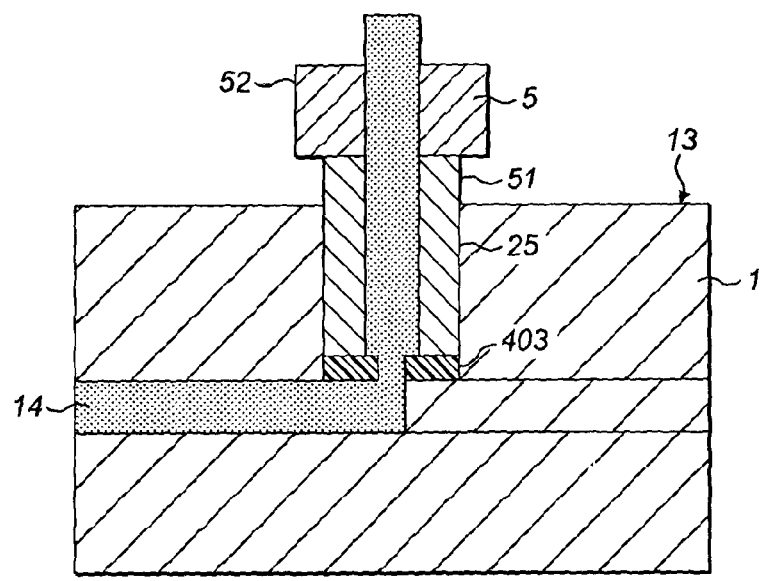

Referring now to FIG. 10, this illustrates the arrangement of an inlet or outlet connector 5 in certain embodiments of the invention. The connector 5 comprises a first cylindrical portion 51 of a first diameter, and a second cylindrical portion 52 of a second, greater diameter. The first cylindrical portion 51 is received within the corresponding bore or access hole 25 in the block 1 of the micro rheometer. A central bore extends through both portions of the connector, generally along its longitudinal axis, and is in fluid communication with the flow channel 14 by means of a hole, aperture or bore in another fringeless hard rubber seal 403 compressed between an axial end of the connector 5 and a surface of the block 1.

Figure 11:
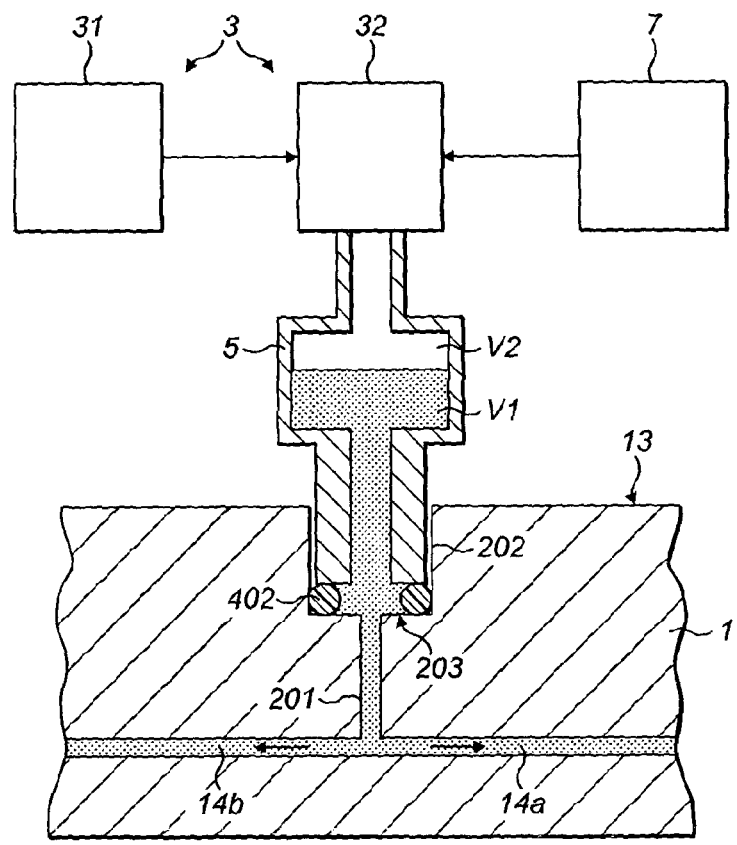
FIG. 11 is a schematic representation of part of another rheometer embodying the invention.

Referring now to FIG. 11, this illustrates part of a rheometer embodying the invention. The rheometer comprises a block 1 with two flow channels 14a, 14b defined within it. An access hole extends from a point connecting the two flow channels upwardly through the block to an upper surface 13. This hole comprises a lower portion 201 in direct communication with the flow channels and an upper portion 202 which is substantially wider than the lower portion 201. This upper portion 202 is substantially cylindrical, and a shoulder portion 203 connects the upper and lower portions, 201, 202. A reservoir 5 adapted to hold a volume V1 of test fluid is fixed in the hole, that is fixed into the upper portion 202 of the hole by suitable means. In certain embodiments this fixing is via threads provided on the reservoir outer surface and the internal surface of the hole, although in other embodiments alternative fixing means may be employed. For example, in certain embodiments then reservoir 5 may be adapted to be a push fit into the hole (e.g. an interference fit). An end surface of the reservoir 5 compresses an o-ring 402 against the shoulder 203 of the hole so as to form a seal. The reservoir 5 is adapted to hold a volume V1 of test fluid in the range 0.1 to 2 ml, for example 1 ml. The apparatus also comprises pumping means 3 in the form of a pressure pump. This pressure pump comprises a high pressure source 31, such as a cylinder of compressed gas. This high pressure source 31 is connected to a controllable regulator 32 under the control of a controller 7. The controllable regulator 32 is connected to the reservoir 5 and determines a pressure of a volume V2 of fluid inside the reservoir and in contact with a surface of the volume of test fluid. The controller 7 controls the controllable regulator 32 to set the pressure of this volume of fluid V2 in the reservoir 5, and in this particular embodiment the pressure is controllable to any value up to the pressure of the high pressure source 31. Thus, the pressure pumping means sets a pressure applied to the test fluid and, by applying this pressure to the test fluid, causes test fluid to flow simultaneously along flow channels 14A and 14B. Thus, fluid flow can be driven with a constant pressure, if desired. The drive pressure in turn determines the flow rate of fluid through the plurality of flow channels. Although two flow channels are shown in the figure, in alternative embodiments the pressure pump may drive fluid flow in just a single channel, or along an even greater number of flow channels simultaneously. Advantageously, this pressure drive enables steady state flow conditions to be achieved rapidly, hence requiring only small volumes of sample (i.e. test) fluid. As steady state conditions are achieved rapidly, only small volumes of sample fluid may be consumed in arriving at that steady state condition. This pressure drive is in contrast to alternative embodiments in which the pumping means is arranged to displace some actuating membrane in contact with the test fluid so as to determine flow rate. Such simples include syringe pumps and piezo electric pumps. In such embodiments, where flow rate is controlled, the resultant pressure in the system is determined by flow rate. The pressure drive system shown in FIG. 11 is particularly convenient for the testing of small samples of biological material. Thus, embodiments of the invention may be used in diagnostic applications, such as medical diagnostics.

Figure 12:
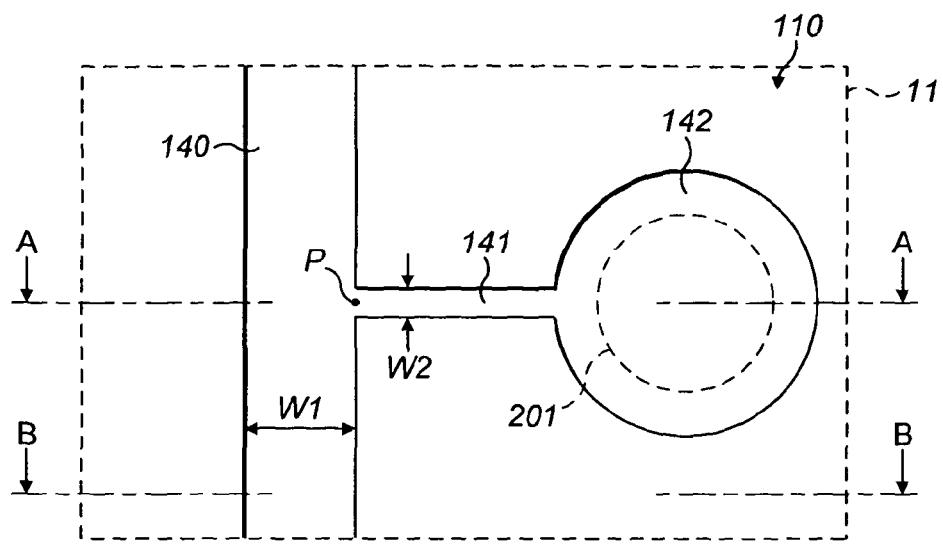
FIG. 12 is a schematic view, from above, of part of rheometry apparatus embodying the invention.

Referring now to FIG. 12, this is a schematic view, from above, of part of a rheometer embodying the invention. FIG. 12 illustrates part of the upper flat surface 110 of a first block portion 11 which has a recess defining a flow channel 140 formed in it. This flow channel 140 has been defined by a lithographic technique in this example, comprising conventional masking and etching techniques. This channel 140 in the illustrated portion has constant width W1. At the same time as the flow channel 140 was fabricated, a side channel 141 and side chamber 142 (which may also be referred to as a chamber portion of the relevant hole or access hole in the block) have been formed. The side channel 141 has a width W2 which is much smaller than W1 in this example (e.g. less than 10% of the width W1, or even smaller) and a mouth of the side channel 141 communicates with the flow channel 140 generally at position P. The opposite end of the side channel 141 joins the side chamber 142 which in this example is provided by a generally circular recess in the surface 110 of the first block portion 11. In alternative embodiments, the side chamber 142 may have different shapes. Conveniently, however, the side chamber 142 is substantially wider than the side channel 141. As will be appreciated, the side channel 141 provides a substantial constriction between the flow channel 140 and the side chamber 142. Also shown in the figure is a broken line 201 illustrating the position of a first portion 201 of a hole through the upper block portion 12 relative to the side chamber 142 when the two block portions are attached together. As will be appreciated, the first hole portion 201 has a diameter which is substantially larger than the width of the side channel 141. Advantageously, provision of the side chamber 142 facilitates manufacture. Provided the hole in the upper block portion can be manufactured with sufficient accuracy so that it at least partly overlaps with the side chamber 142 when the two block portions are attached together, then the hole in the upper block will be in fluid communication with the side channel 141 and hence position P of the flow channel 140.

Figure 13:
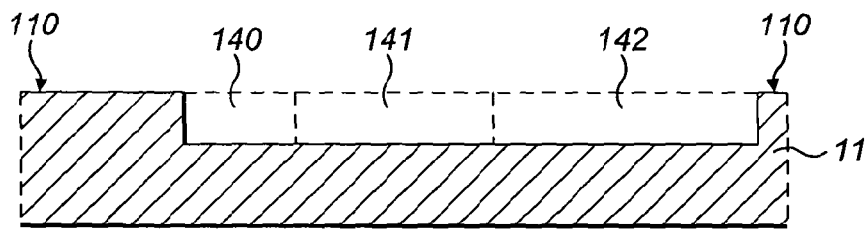
FIG. 13 is a schematic representation of the cross section of the apparatus of FIG. 12 along line A-A.
Figure 14:
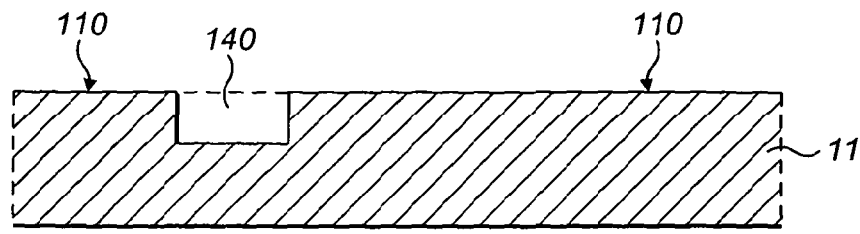
FIG. 14 is a schematic representation of a cross section of the apparatus of FIG. 12 along line B-B.

Referring now to FIG. 13, this shows a cross-section of the part of the lower block shown in FIG. 12 along line A-A. FIG. 14 illustrates a second cross-section, along line B-B.

Figure 15:
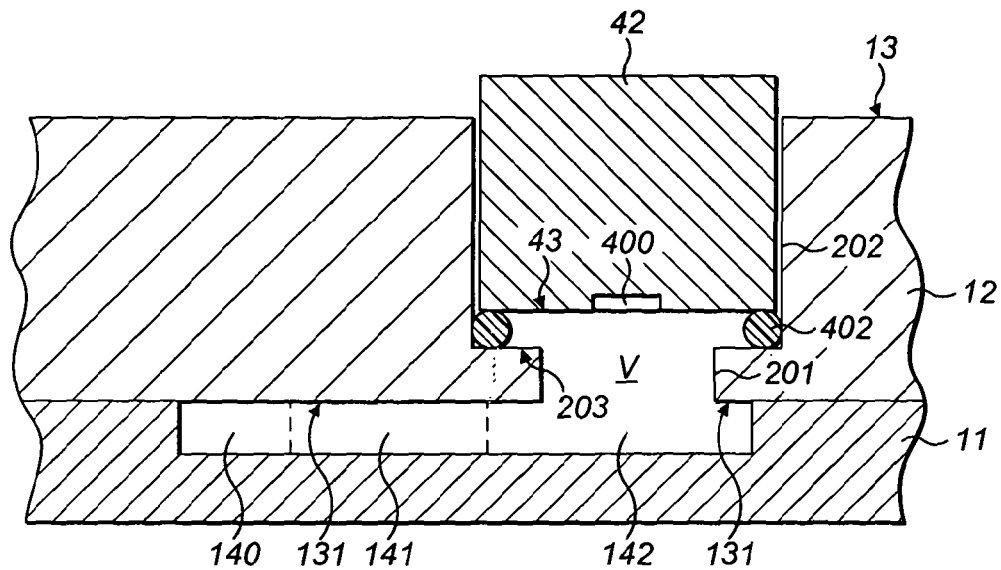
FIG. 15 is a schematic representation of the cross section of the apparatus from FIG. 12 along line A-A with the upper block bonded to it, and a pressure sensor located in a respective hole.

Referring now to FIG. 15, this shows a cross-section of the apparatus with the upper block portion 12 attached to the lower block portion 11 so that the flow channel and side channel are defined between the lower block portion 11 and the flat surface 131 of the upper block portion 12. The upper block portion has a hole formed within it, that hole comprising a lower portion 201, which is aligned so as to provide a mouth which is wholly within the perimeter of the side chamber 142. The hole comprises an upper portion 202 which is slightly wider than the lower portion 201. A flat shoulder portion 203 connects the lower portion 201 to the upper portion 202. Within the upper portion 202 of the hole there is provided a pressure sensor housing 42 having an end surface 43 arranged to engage and compress an o-ring 402 against the shoulder portion 203 of the hole. At this end surface 43 there is also arranged a pressure sensing element 400. The pressure sensor housing 42 thus forms a seal with the upper block portion 12 via the o-ring 402. The pressure sensor element 400 is arranged so that it senses a pressure of a volume of fluid V contained in the sealed space between the pressure sensing housing, o-ring, shoulder portion 203, lower hole portion 201, and the side chamber 142. Thus, the pressure sensor element 400 is able to sense fluid pressure in this volume V, which is in communication, via the side channel 141, with point P in the flow channel 140. Advantageously, the width of the side channel 141 can be made very small so as not to perturb flow conditions in the flow channel 140, the hole in the upper block can be made large enough to facilitate arrangement of a pressure sensor within it, and provision of the side chamber 142 facilitates mating of the portion of the hole defined in the upper block portion 12 with the part of the access hole provided by the side channel 141 and side chamber 142. As will be appreciated, the side channel 141 and side chamber 142 form portions of an access hole which extends generally along the interface between the upper and lower blocks. The remainder of the access hole is provided in the upper block portion 12, and extends generally upwards from the plane of the flow channel to the block upper surface 13.

Although just a single side channel and single side chamber are shown in the figure, it will be appreciated that embodiments may comprise a plurality of side channels, and optionally side chambers, each tapping in to the flow channel at a respective position to enable a fluid property at that position to be measured, without disturbing fluid flow along the flow channel.

Figure 16:
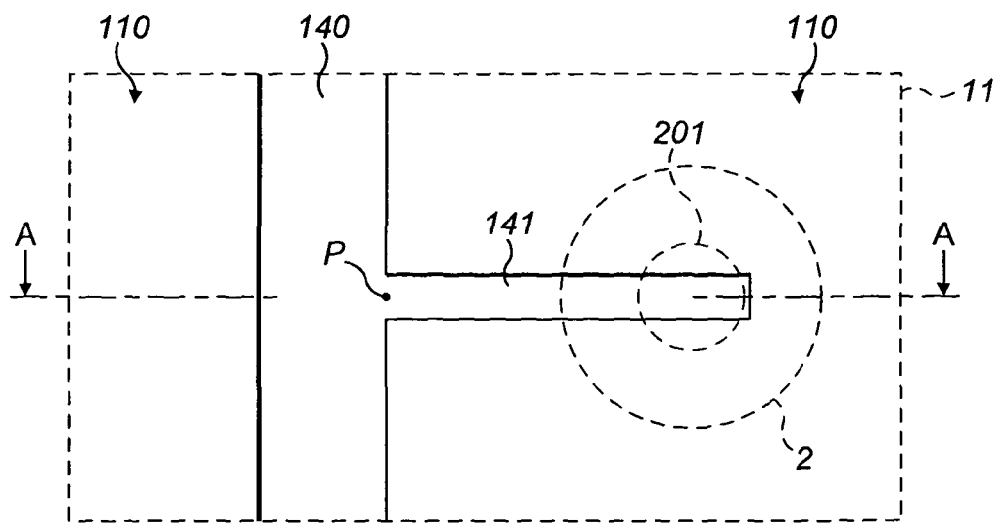
FIG. 16 is a schematic view, from above, of part of other rheometry apparatus embodying the invention.
Figure 17:
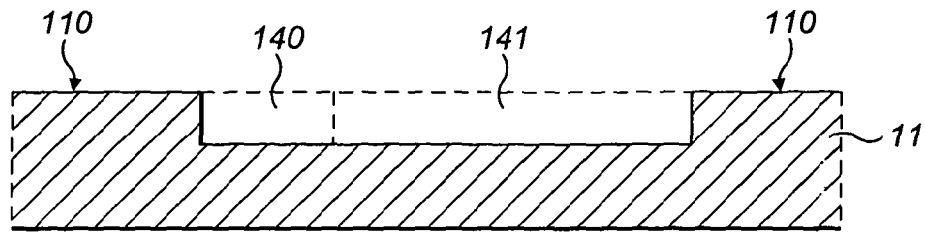
FIG. 17 is a schematic representation of the cross section of the apparatus from FIG. 16, along line A-A.

Referring now to FIG. 16, this shows part of an alternative embodiment generally having the same construction as the apparatus shown in FIG. 12, but differing in that the side channel 141 does not widen out into a side chamber. FIG. 17 shows a cross-section along line A-A. In order for the upper block portion 12 to be correctly aligned with the lower block portion 11, then a mouth of a hole provided through the upper block portion 12 must at least partially overlap the side channel 141 when the two block portions are attached together. If the hole of the upper block portion 12 has a relatively small mouth (represented by broken line 201 in the figure) then the positioning of the upper block portion 12 relative to the lower block portion 11 and/or the manufacturing of the mouth in the upper portion must be performed with high accuracy. This is achieved in certain embodiments. However, in alternative embodiments, the hole 2 in the upper block portion 12 is arranged to have a relatively wide mouth, illustrated by broken line 2 in FIG. 16. By arranging the hole to have a relatively wide mouth, the demands on upper block positioning relative to the lower block, and accuracy of positioning of the hole in the upper block are reduced.

Figure 18:
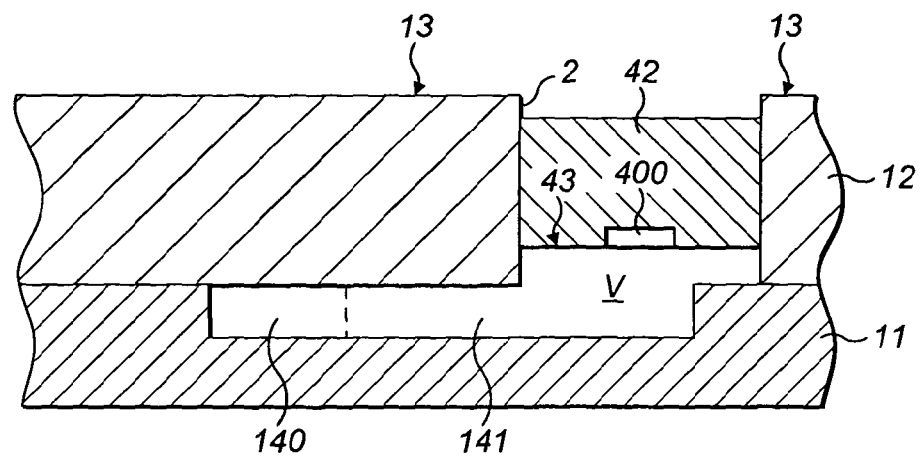
FIG. 18 is a schematic representation of the cross section of the apparatus from FIG. 16 along line A-A with an upper block portion bonded in place.

Referring to FIG. 18, this shows the upper block portion 12 with the hole 2 having a relatively wide mouth being attached to the lower block portion 11. There is considerable overlap between the side channel 141 and the hole 2 and hence a pressure sensor 400 housed in the hole 2 is in communication with the volume of fluid V filling the side channel 141. Again, the pressure sensor 400 can be relatively large, and is able to sense a pressure of fluid at a point P in the flow channel 140 via the constricted side channel 141. In the arrangement show in FIG. 18, the pressure sensing housing 42 forms a seal against internal side wall of the hole 2 through the upper block portion 12, and no o-ring is required.

It will be appreciated that embodiments of the invention may comprise one or more micro fluidic channels and enable the rheometric characterisation of complex fluids. Certain embodiments may be used to measure steady shear and extensional viscosity.

In certain embodiments, the pumping means may be a syringe or positive displacement pump. However, alternative forms of pumping means may also be employed, such as piezo electric actuators. Embodiments of the invention may incorporate a wide variety of sensors, such as pressure sensors, temperature sensors, and other sensors for measuring fluid properties.

Certain embodiments comprise a flow channel or flow channel network having a cross-slit flow geometry for measuring extensional viscosity.

Certain embodiments may be described as rheo-chip rheometers, designed for full rheometric and flow characterisation of complex fluids in microscopic flow. Such embodiments not only measure steady shear and nominal extensional viscosity, but may also be used to measure storage and loss moduli by performing small or large amplitude oscillatory experiments (SAOS or LAOS) with frequencies up to 1000 Hz or even higher. Certain embodiments have modular design, and incorporate miniaturised high precision piezo electric actuators for SAOS and/or LAOS experiments, as well as, or as an alternative to, syringe or other positive displacement pumps for steady flow experiments.

Certain embodiments may be described as micro fluidic chips made of rigid plastic or fused silica materials which are suitable for massive production in a highly cost effective way without compromising performance. By having modular design, embodiments of the invention comprising a rheo-chip and a variety of interchangeable sensors, embodiments of the invention are able to provide great flexibility in terms of the deployment of sensors at various interrogation points along a variety of flow geometries in a cost-effective way without compromising performance.

Certain embodiments may be used to measure the shear viscosity of whole blood. Certain embodiments may also be used with optical techniques to determine the aggregation of whole blood cells.

A range of pressure sensors may be used in embodiments of the invention (for example, pressure sensors enabling pressure measurements up to 15 Bar may be used) and can be readily deployed and interchanged without requiring any change in the rheo-chip or block into which they are connected.

In certain embodiments, the entire flow geometry of the chip or block is easily accessed by in-situ rheo-optical probes including micro-piv, flow-induced birefringence measurements, fluorescent and polarised microscopy, laser tweezers with multiple optical traps etc.

Certain embodiments comprise a rheometer block with a flow channel having a cross-slit flow geometry such that extensional flow around a stagnation point may be generated, thereby providing reliable measurement of "true" steady state extensional viscosity of complex fluids.

Certain embodiments of the invention can be used for simultaneously performing rheometric characterisation of complex fluids in a range of different flow rates or different frequencies and/or amplitudes in small-amplitude oscillatory shear (SAOS) or large-amplitude oscillatory shear (LAOS).

Certain embodiments of the invention can be used for cell-plasma separation and simultaneous measurement of the rheological properties of whole blood and plasma.

In certain embodiments, a biosensor or biosensors can be integrated into the block or chip to enable simultaneous biological analysis and rheometric characterisation.

Certain embodiments of the invention take the form of microfluidic chips, and can be utilised in quality and processing control in the production of biofluids such as DNA, protein and cellular (stem cells)

Certain embodiments of the invention take the form of microfluidic chips, and can be utilised in productions of uniform size microemulsions and fibres.

Certain embodiments of the invention provide rheometry apparatus which enable the entire system to be reduced in size. For example, certain embodiments provide rheometer chips or blocks which are suitable for mounting on microscopes for in-situ structural characterisation, or which can be used in space stations for carrying out rheometric characterisation in zero gravity.

Certain embodiments provide rheometry systems which are fully automated to enable high-throughout rheological analysis of a large number of samples (e.g. measuring a plurality of samples simultaneously).

It will be appreciated that the block or block structure of embodiments of the invention described above may also be described as a rheo-chip. Thus, certain embodiments of the invention provide a rheo-chip based rheometer.

Certain embodiments represent the miniaturisation of a desktop rheometer into a rheo-chip-based, and palm sized micro rheometer.

Certain rheometers embodying the invention can perform full rheometric and flow characterisation of complex fluids in microscopic flow and can be used in novel mechanical spectroscopy techniques for the characterisation of complex fluids.

Certain rheo-chips embodying the invention are made of rigid plastic or fused silica materials with high precision flow channels defined therein. Such embodiments are suitable for mass production in a highly cost-effective way without compromising performance.

Embodiments of the present invention are able to provide a number of advantages/benefits, including the following:

Certain embodiments are able to provide measurement of non-linear steady shear viscosity and extensional viscosity of complex fluids at deformation rates at least two orders of magnitude higher than those of commercial rheometers, that is up to $10^6$ $s^{-1}$ or higher.

Embodiments of the invention are able to be used to measure storage and loss moduli at frequencies at least two orders of magnitude higher than those of currently available commercial rheometers, that is up to 1000 Hz or higher.

In certain embodiments of the invention the flow channel (or flow channels) is arranged to have a sufficiently small volume that inertial effects are minimised, or even completely eliminated.

Certain embodiments provide the advantage of enabling high sensitivity measurements to be made, and require only a very small amount of sample (e.g. no more than 1 or a few micro liters).

Embodiments of the invention provide the advantage of giving high flexibility in the deployment of sensors at required/selected interrogation points along the micro flow geometry.

Certain embodiments also provide the advantage that the fluid flowing within the channel or channels is easily accessible by optical probes.

Certain embodiments also provide the advantage that they enable high through-put rheological characterisation.

In contrast to embodiments of the present invention, certain known commercial rheometers are limited by the mechanical actuator they employ and the inertial effects at rather low deformational rates (about 5000 s$^{-1}$) and low frequencies (about 30 Hz). Certain known micro fluidic-based viscometers can only measure non-linear shear viscosity, using conventional syringe pumps and expensive pressure sensors limited up to just 2 Bar. Certain embodiments of the invention are thus able to fulfil the need for rheometry apparatus able to provide full rheological and flow characterisation.

As mentioned above, certain rheo-chips embodying the invention are made from PMMA, and may be fabricated by soft lithographic methods. In other words, lithographic techniques may be used to form the channels in one part of the rheo-chip or block, which cooperates with the other part or parts to define the internal flow channels.

Certain embodiments employ pumping means in the form of high precision piezo electric actuators, as well as, or as an alternative to, conventional syringe pumps.

It will be appreciated that the fluid channels incorporated in embodiments of the invention may have a variety of widths, depths, shapes, aspect ratios, lengths etc. For example, suitable approximate channel widths (for example of unconstricted portions) include, but are not limited to: 2 mm; 1.5 mm; 1 mm; 0.80 mm; 0.50 mm; 0.10 mm; 0.050 mm; 0.045 mm; 0.040 mm; and even smaller. Suitable approximate channel depths include, but are not limited to: 2 mm; 1.5 mm; 1 mm; 0.80 mm; 0.50 mm; 0.10 mm; 0.062 mm; 0.050 mm; 0.045 mm; 0.040 mm; and even smaller. Suitable channel shapes include, but are not limited to, rectangular and square. Suitable aspect ratios of rectangular channels (width:depth) include, but are not limited to: 8:1; 6:1; 4:1; 2:1; 1:1; 1:0.5; 1:0.33; 1:0.25; and 1:0.2. Suitable channel lengths include, but are not limited to: 100 mm; 80 mm; 60 mm; 40 mm; 20 mm; and even shorter. Suitable lengths of constricted portions include, but are not limited to: 60 mm; 40 mm; 20 mm; 10 mm; 5 mm; and even shorter. In certain embodiments, constricted portions are constricted in just one dimension compared with unconstricted portions, e.g. in just width or just depth. In certain alternative embodiments, constricted portions are constricted in two dimensions, i.e. in both width and depth. Suitable constriction ratios (e.g. of unconstricted width to constricted width) include, but are not limited to: 10:1; 8:1; 6:1; 4:1; and 2:1. Any possible combination of the above-mentioned specific dimensions, aspect ratios, and/or constriction ratios may be employed in embodiments of the invention.

The invention claimed is:

1. A microfluidic rheometry apparatus for use in microfluidic rheometry, the apparatus comprising:
a block of substantially rigid material having an external surface and at least a first internal flow channel, the first internal flow channel being arranged inside the block and substantially in a plane and the block further comprising a plurality of holes, each hole communicating with the first internal flow channel at a respective position along the first internal flow channel and extending from the respective position to said external surface so as to provide access to the first internal flow channel from the external surface, the plurality of holes comprising a first hole communicating with a first said position, for connection to pumping means to drive fluid flow along said first internal flow channel, a second hole communicating with a second position and in which a sensor may be located to measure a property of fluid at the second position, and a third hole, communicating with a third position, adapted to receive a sensor to measure a property of fluid at the third position;
wherein at least one of the plurality of holes comprises a first portion adjacent the first internal flow channel and a second portion adjacent the external surface, the first portion providing a constriction between the first internal flow channel and the second portion.

2. Apparatus in accordance with claim 1, wherein the plurality of holes comprises a fifth hole communicating with a fifth position to introduce fluid into the flow channel.

3. Apparatus in accordance with claim 1, wherein the plurality of holes comprises a sixth hole communicating with a sixth position and via which fluid may be extracted or expelled from the flow channel.

4. Apparatus in accordance with claim 1, wherein at least a portion of each of the plurality of holes extends in a direction substantially perpendicular to said plane.

5. Apparatus in accordance with claim 1 wherein said block is substantially transparent to visible light.

6. Apparatus in accordance with claim 1, wherein said block is formed from PMMA or fused silica.

7. Apparatus in accordance with claim 1, wherein said external surface is substantially flat.

8. Apparatus in accordance with claim 1, wherein the first internal flow channel comprises a cruciform feature having four arms and the plurality of holes comprises four holes arranged for accommodating pressure sensors to measure the pressure of fluid flowing in each arm of the cruciform feature.

9. Apparatus in accordance with claim 1, wherein the first internal flow channel comprises a plurality of flow-affecting features arranged in series such that pumping means connected to the first hole can drive fluid flow through the plurality of flow-affecting features simultaneously, the plurality of holes being arranged so as to permit sensors to be located to measure at least one property of fluid flow at, along, or across each flow-affecting feature.

10. Apparatus in accordance with claim 1, further comprising:
a pressure sensor arranged inside the third hole to measure the pressure of fluid within the third hole and in communication with the third position.

11. Apparatus in accordance with claim 1, wherein the first flow channel has a volume less than 5 ml.

12. Apparatus in accordance with claim 1, further comprising:
an automated loading system for loading fluid into the or each fluid channel.

13. Apparatus in accordance with claim 1, wherein the plurality of holes comprises a fourth hole communicating with a fourth position for connection to reservoir means adapted to hold a reservoir of fluid.

14. Apparatus in accordance with claim 13, wherein said fourth position is downstream of the second and third positions relative to the first position.

15. Apparatus in accordance with claim 13, further comprising: reservoir means connected to the fourth hole and arranged to hold a volume of liquid in communication with the first flow channel.

16. Apparatus in accordance with claim 1, wherein said block comprises a plurality of separate internal flow channels, including said first internal flow channel, and a respective plurality of holes communicating with different positions along each separate flow channel, whereby the block may be used to measure at least one rheological property of a plurality of separate fluid samples simultaneously, each fluid sample being located in a respective one of the separate flow channels.

17. Apparatus in accordance with claim 16, wherein each of the plurality of separate internal flow channels has the same geometry.

18. Apparatus in accordance with claim 1, wherein each of said plurality of holes is threaded.

19. Apparatus in accordance with claim 18 wherein the first portion is connected to the second portion by at least a shoulder against which an 'O' ring may be compressed to form a seal.

20. Apparatus in accordance with claim 18, wherein the first portion is generally cylindrical.

21. Apparatus in accordance with claim 20, wherein the first portion has a diameter smaller than a width of the flow channel at the position at which the hole is in communication with the flow channel.

22. Apparatus in accordance with claim 18, wherein the first portion comprises a side channel extending from a side of the flow channel and substantially in said plane.

23. Apparatus in accordance with claim 22, wherein the side channel has a width smaller than a width of the flow channel at the position where the side channel communicates with the flow channel.

24. Apparatus in accordance with claim 22, wherein the side channel extends from the flow channel to a chamber portion of the respective hole, the chamber portion providing a chamber extending generally in said plane for containing a volume of fluid in communication, via the side channel, with the flow channel.

25. Apparatus in accordance with claim 18, wherein the second portion is generally cylindrical.

26. Apparatus in accordance with claim 25, wherein the second portion is provided with a screw thread for engagement by a correspondingly threaded portion of a pumping means, sensor housing, reservoir means, or inlet or outlet connector.

27. Apparatus in accordance with claim 1, wherein said block comprises a first block portion and a second block portion, the first internal flow channel being provided at an interface between the first and second block portion, said external surface being an external surface of the second block portion, and each said hole extending from said interface, through the second block portion, to said external surface.

28. Apparatus in accordance with claim 27, wherein a side channel extends from the flow channel to a chamber portion of the respective hole, the chamber portion providing a chamber extending generally in said plane for containing a volume of fluid in communication, via the side channel, with the flow channel, and wherein said side channel, and optionally said chamber portion, is provided at said interface.

29. Apparatus in accordance with claim 28, wherein said first internal flow channel has been formed by forming a recess in a flat surface of the first block portion and attaching a flat surface of the second block portion to said flat surface of the first block portion.

30. Apparatus in accordance with claim 29, wherein said side channel, and optionally said chamber portion, comprises a respective recess in said flat surface of the first block portion.

31. Apparatus in accordance with claim 1, wherein said first internal flow channel comprises a constricted portion.

32. Apparatus in accordance with claim 31, wherein the second and third positions are located on either side of the constricted portion.

33. Apparatus in accordance with claim 31, wherein the second and third positions are each located along the constricted portion.

34. Apparatus in accordance with claim 1, wherein said block comprises a network of internal flow channels arranged substantially in said plane, said network including the first internal flow channel.

35. Apparatus in accordance with claim 34, wherein the first position is arranged such that pumping means connected to the first hole can drive fluid flow through said network, and the plurality of holes being arranged to permit location of sensors to measure at least one property of fluid flow at a plurality of positions over said network.

36. Apparatus in accordance with claim 1, further comprising:
pumping means connected to said first hole for driving fluid flow along said first flow channel.

37. Apparatus in accordance with claim 36, wherein the pumping means is operable to drive at least one of steady flow and oscillatory flow.

38. Apparatus in accordance with claim 36, wherein the pumping means is operable to generate suction to draw a sample of fluid into the flow channel via a hole other than the first hole.

39. Apparatus in accordance with claim 36, wherein the pumping means is adapted to drive said fluid flow by applying a controlled pressure.

40. Apparatus in accordance with claim 1, further comprising:
a pressure sensor arranged inside the second hole to measure the pressure of fluid within the second hole and in communication with the second position.

41. Apparatus in accordance with claim 40, wherein the pressure sensor is attached to a pressure sensor housing having an external screw thread engaged by a corresponding internal screw thread of the second hole.

42. Apparatus in accordance with claim 41, further comprising sealing means arranged to prevent fluid flow from the first channel out of the second hole.

43. Apparatus in accordance with claim 42, wherein the sealing means comprises an O ring arranged to form a seal between a surface of the pressure sensor housing and an internal surface of the second hole.

44. Apparatus in accordance with claim 43, wherein the 0 ring is arranged to be compressed between an end surface of the pressure sensor housing and a shoulder of the second hole when the housing is screwed into the second hole.

45. A method of manufacturing a rheometer, the method comprising:
providing a first body of substantially rigid material having a flat surface;
forming at least one channel in said flat surface;
providing a second body of substantially rigid material having a flat surface, for mating with the flat surface of the first body, and an external surface;
forming a plurality of holes through the second body, from the flat surface to the external surface, at selected positions;
mating said flat surfaces together such that at least a first internal flow channel is defined by said at least one channel in the flat surface of the first body and the flat surface of the second body, and such that each hole communicates with the first internal flow channel at a respective position along the first internal flow channel so as to provide access to the first internal flow channel from said external surface, whereby the holes are adapted to connect a pumping means and sensing means to the holes to drive fluid flow along the first internal flow channel and measure one or more properties of fluid flowing along the first internal flow channel;

wherein at least one of the plurality of holes comprises a first portion adjacent the flow channel and a second portion adjacent the external surface, the first portion providing a constriction between the flow channel and the second portion.

46. A method in accordance with claim 45, further comprising bonding said flat surfaces together.

47. A method in accordance with claim 46, wherein the first and second bodies are each formed from a thermoplastic material, and said bonding comprises thermal bonding.

48. A method in accordance with claim 45, further comprising positioning a pressure sensing element inside a said hole.

49. A method in accordance with claim 48, further comprising:
   providing a constriction between the pressure sensing element and the first flow channel.

50. A method of manufacturing a rheometer, the method comprising:
   providing a first body of substantially rigid material having a flat surface;
   forming a channel, a side channel extending from a side of the channel, and optionally a side chamber at an end of the side channel, in said flat surface;
   providing a second body of substantially rigid material having a flat surface, for mating with the flat surface of the first body, and an external surface;
   forming a hole through the second body, from the flat surface to the external surface;
   mating said flat surfaces together such that an internal flow channel is defined by said channel and the flat surface of the second body, and such that said hole communicates with either the side channel or the side chamber, whereby said hole being adapted to receive a sensing means to measure a property of fluid flowing along the flow channel;
   wherein at least one of the plurality of holes comprises a first portion adjacent the flow channel and a second portion adjacent the external surface, the first portion providing a constriction between the flow channel and the second portion.

51. A method in accordance with claim 45 or claim 50, further comprising providing the or each hole with a respective internal screw thread.

* * * * *